(12) United States Patent
Gottlieb et al.

(10) Patent No.: US 9,215,995 B2
(45) Date of Patent: Dec. 22, 2015

(54) SENSOR SYSTEMS HAVING MULTIPLE PROBES AND ELECTRODE ARRAYS

(75) Inventors: Rebecca K. Gottlieb, Culver City, CA (US); Chia-Hung Chiu, Granada Hills, CA (US); Meena Ramachandran, San Francisco, CA (US); Nandita Dangui-Patel, Los Angeles, CA (US); Jefferson Rose, Culver City, CA (US); Ashwin K. Rao, Northridge, CA (US); Hsifu Wang, Northridge, CA (US); Ying Luo, Stevenson Ranch, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 842 days.

(21) Appl. No.: 13/165,061

(22) Filed: Jun. 21, 2011

(65) Prior Publication Data

US 2011/0319734 A1    Dec. 29, 2011

Related U.S. Application Data

(60) Provisional application No. 61/357,803, filed on Jun. 23, 2010, provisional application No. 61/385,418, filed on Sep. 22, 2010.

(51) Int. Cl.
| | |
|---|---|
| A61B 5/05 | (2006.01) |
| A61B 5/1486 | (2006.01) |
| A61B 5/145 | (2006.01) |
| C12Q 1/00 | (2006.01) |
| A61B 5/00 | (2006.01) |
| G01N 27/30 | (2006.01) |

(52) U.S. Cl.
CPC ............ *A61B 5/1486* (2013.01); *A61B 5/14503* (2013.01); *A61B 5/14532* (2013.01); *C12Q 1/001* (2013.01); *A61B 5/0017* (2013.01); *A61B 5/726* (2013.01); *G01N 27/307* (2013.01)

(58) Field of Classification Search
USPC .................................................. 600/345, 347
See application file for complete search history.

(56) References Cited

U.S. PATENT DOCUMENTS

| | | | |
|---|---|---|---|
| 4,562,751 | A | 1/1986 | Nason et al. |
| 4,573,994 | A | 3/1986 | Fischell et al. |
| 4,678,408 | A | 7/1987 | Nason et al. |

(Continued)

FOREIGN PATENT DOCUMENTS

| | | |
|---|---|---|
| EP | 0980687 | 2/2000 |
| EP | 1413245 | 4/2004 |

(Continued)

OTHER PUBLICATIONS

International Search Report mailed on Feb. 6, 2012 for international application No. PCT/US2011/041357 filed on Jun. 22, 2011.

(Continued)

*Primary Examiner* — Michael Kahelin
*Assistant Examiner* — Mitchell E Alter
(74) *Attorney, Agent, or Firm* — Gates & Cooper LLP

(57) ABSTRACT

Embodiments of the invention provide amperometric analyte sensors having multiple related structural elements (e.g. sensor arrays comprising a working, counter and reference electrode) and algorithms designed for use with such sensors. While embodiments of the innovation can be used in a variety of contexts, typical embodiments of the invention include glucose sensors used in the management of diabetes.

24 Claims, 11 Drawing Sheets

Procedure of sensor fusion

(56) References Cited

U.S. PATENT DOCUMENTS

| | | |
|---|---|---|
| 4,680,268 A | 7/1987 | Clark, Jr. |
| 4,685,903 A | 8/1987 | Cable et al. |
| 4,755,173 A | 7/1988 | Konopka et al. |
| 4,953,552 A * | 9/1990 | DeMarzo ................ 600/347 |
| 5,390,671 A | 2/1995 | Lord et al. |
| 5,391,250 A | 2/1995 | Cheney, II et al. |
| 5,485,408 A | 1/1996 | Blomquist |
| 5,505,713 A | 4/1996 | Van Antwerp |
| 5,522,803 A | 6/1996 | Teissen-Simony |
| 5,568,806 A | 10/1996 | Cheney, II et al. |
| 5,586,553 A | 12/1996 | Halili et al. |
| 5,665,065 A | 9/1997 | Colman et al. |
| 5,800,420 A | 9/1998 | Gross et al. |
| 5,807,375 A | 9/1998 | Gross et al. |
| 5,851,197 A | 12/1998 | Marano et al. |
| 5,925,021 A | 7/1999 | Castellano et al. |
| 5,954,643 A | 9/1999 | VanAntwerp et al. |
| 5,968,011 A | 10/1999 | Larsen et al. |
| 6,017,328 A | 1/2000 | Fischell et al. |
| 6,086,575 A | 7/2000 | Mejslov |
| 6,093,172 A | 7/2000 | Funderburk et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,293,925 B1 | 9/2001 | Safabash et al. |
| 6,355,021 B1 | 3/2002 | Nielsen et al. |
| 6,379,301 B1 | 4/2002 | Worthington et al. |
| 6,461,329 B1 | 10/2002 | Van Antwerp et al. |
| 6,475,196 B1 | 11/2002 | Vachon |
| 6,484,045 B1 | 11/2002 | Holker et al. |
| 6,544,212 B2 | 4/2003 | Galley et al. |
| 6,554,798 B1 | 4/2003 | Mann et al. |
| 6,558,351 B1 | 5/2003 | Steil et al. |
| 6,591,876 B2 | 7/2003 | Safabash |
| 6,607,509 B2 | 8/2003 | Bobroff et al. |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,770,729 B2 | 8/2004 | Van Antwerp |
| 6,801,420 B2 | 10/2004 | Talbot et al. |
| 6,804,544 B2 | 10/2004 | Van Antwerp et al. |
| 6,809,653 B1 | 10/2004 | Mann et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2001/0053891 A1 | 12/2001 | Ackley |
| 2002/0032374 A1 | 3/2002 | Holker et al. |
| 2003/0050575 A1 | 3/2003 | Diermann et al. |
| 2003/0199837 A1 | 10/2003 | Vachon |
| 2003/0208154 A1 | 11/2003 | Close et al. |
| 2005/0004439 A1 | 1/2005 | Shin |
| 2005/0107743 A1 | 5/2005 | Fangrow, Jr. |
| 2005/0131346 A1 | 6/2005 | Douglas |
| 2006/0253085 A1 | 11/2006 | Geismar et al. |
| 2006/0253086 A1 | 11/2006 | Moberg et al. |
| 2007/0123819 A1 | 5/2007 | Mernoe et al. |
| 2007/0135698 A1 | 6/2007 | Shah et al. |
| 2007/0191702 A1 | 8/2007 | Yodfat et al. |
| 2007/0191771 A1 | 8/2007 | Moyer |
| 2007/0235331 A1 * | 10/2007 | Simpson et al. ......... 204/403.01 |
| 2008/0161664 A1 | 7/2008 | Mastrototaro |
| 2009/0062767 A1 | 3/2009 | Van Antwerp et al. |
| 2009/0192751 A1 | 7/2009 | Kamath |
| 2010/0160861 A1 | 6/2010 | Causey, III et al. |
| 2010/0169035 A1 | 7/2010 | Liang |
| 2010/0280348 A1 * | 11/2010 | Wenzel et al. ................ 600/365 |

FOREIGN PATENT DOCUMENTS

| | | |
|---|---|---|
| EP | 1502613 | 2/2005 |
| JP | 06-507828 | 9/1994 |
| JP | 2000-500380 | 1/2000 |
| JP | 2002536038 | 10/2002 |
| JP | 2008-506468 | 3/2008 |
| JP | 2008-544763 | 12/2008 |
| JP | 2009-521997 | 6/2009 |
| JP | 2009-544407 | 12/2009 |
| JP | 2010-512868 | 4/2010 |
| JP | 2010-518890 | 6/2010 |
| WO | 0045696 | 8/2000 |
| WO | 03074107 | 9/2003 |
| WO | 2004/034032 | 4/2004 |
| WO | 2004030726 | 4/2004 |
| WO | 2005/065542 | 7/2005 |
| WO | 2006102412 | 9/2006 |
| WO | 2007010522 | 1/2007 |
| WO | 2007070486 | 6/2007 |
| WO | 2009032588 | 3/2009 |
| WO | 2010/014959 | 2/2010 |
| WO | 2010/031059 | 3/2010 |

OTHER PUBLICATIONS

Japanese Office Action (with English translation) dated Apr. 28, 2015 for Japanese Patent Application No. 2013-516712.

* cited by examiner

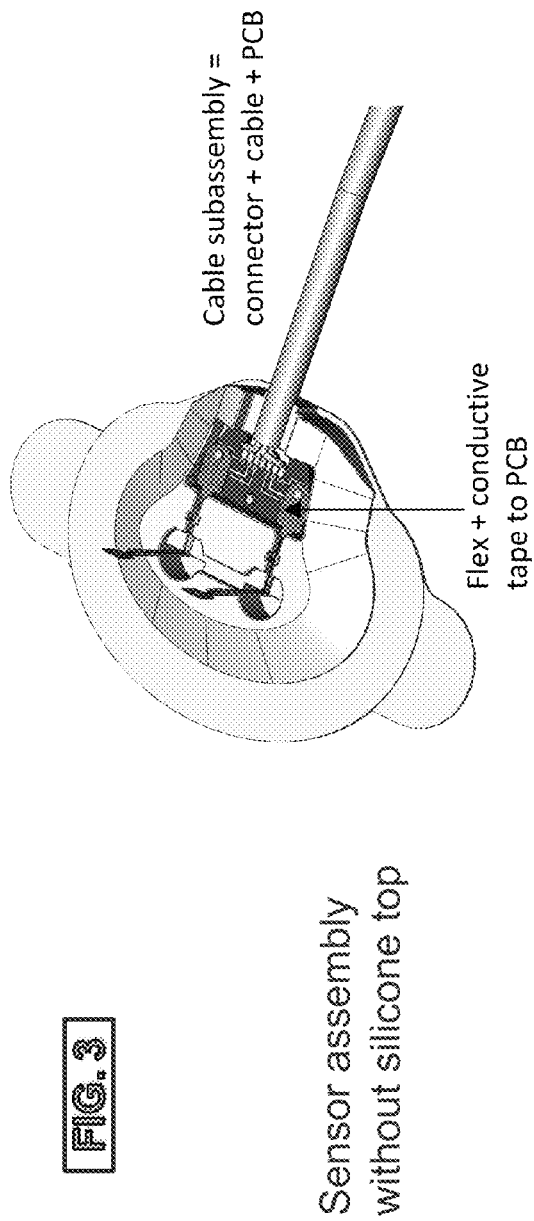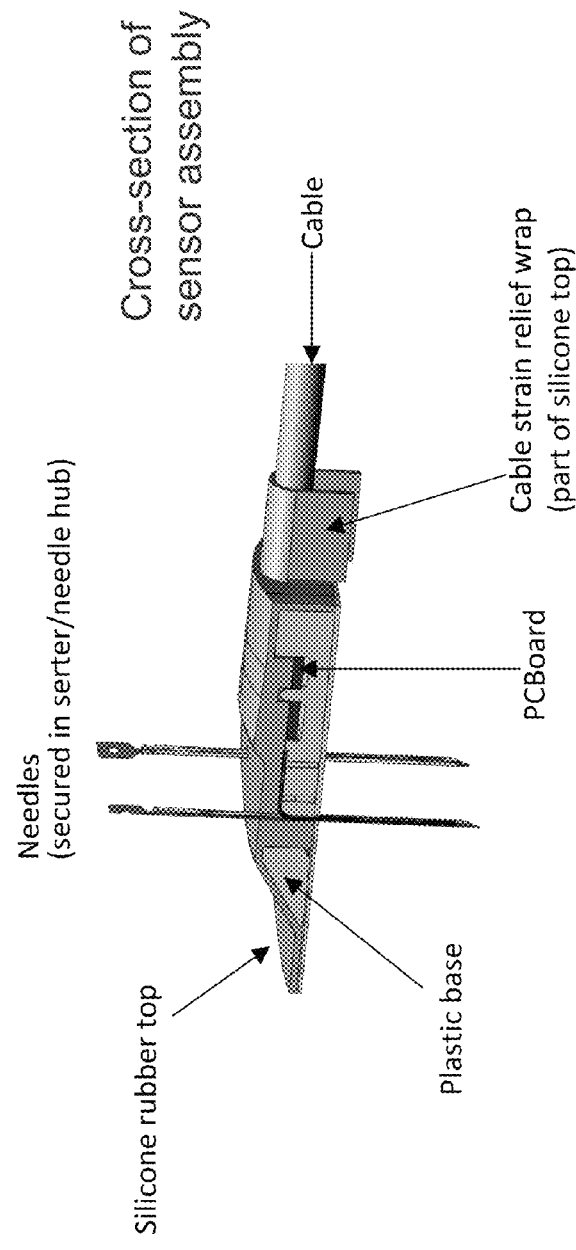

- Each sensor probe has 2 electrode arrays
- Each electrode array is a 3 electrode system with Working, Counter, Reference electrode.
- Total on one Hospital Sensor Assembly is 4 electrode arrays as there are 2 sensor probes.
- 4 independent glucose sensor signals allows for improved system reliability and accuracy through the use of algorithm (sensor fusion).

Calculation of IRI_signal

Procedure of sensor fusion

SENSOR SYSTEMS HAVING MULTIPLE PROBES AND ELECTRODE ARRAYS

CROSS REFERENCE TO RELATED APPLICATIONS

This application claims priority under Section 119(e) from U.S. Provisional Application Ser. No. 61/357,803, filed Jun. 23, 2010; and U.S. Provisional Application Ser. No. 61/385,418 filed Sep. 22, 2010; and claims priority under Section 120 from U.S. application Ser. No. 12/914,969, filed Oct. 28, 2010, the contents of each of which are incorporated herein by reference. This application is related to U.S. patent application Ser. No. 12/572,087, U.S. patent application Ser. No. 11/897,106 and U.S. patent application Ser. No. 12/643,790, the contents of each of which are herein incorporated by reference.

BACKGROUND OF THE INVENTION

1. Field of the Invention

Analyte sensor systems (e.g. glucose sensor systems used in the management of diabetes) and methods and materials for making and using such sensor systems.

2. Description of Related Art

Analyte sensors such as biosensors include devices that use biological elements to convert a chemical analyte in a matrix into a detectable signal. There are many types of biosensors used for a wide variety of analytes. The most studied type of biosensor is the amperometric glucose sensor, which is crucial to the successful glucose level control for diabetes.

A typical glucose sensor works according to the following chemical reactions:

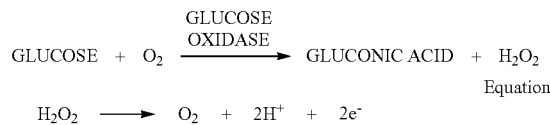

Equation 1

$$H_2O_2 \longrightarrow O_2 + 2H^+ + 2e^-$$

Equation 2

The glucose oxidase is used to catalyze the reaction between glucose and oxygen to yield gluconic acid and hydrogen peroxide (equation 1). The $H_2O_2$ reacts electrochemically as shown in equation 2, and the current can be measured by a potentiostat. These reactions, which occur in a variety of oxidoreductases known in the art, are used in a number of sensor designs.

When a sensor such as a glucose sensor is implanted in a patient, started up and then used to monitor glucose, the glucose sensor may not operate continuously in a stable state. For example, the electrical readings from the sensor, which optimally are directly correlated to the glucose level of the patient, can nonetheless vary and are subject to factors which confound sensor readings, for example erroneous reading that can result from phenomena such as suboptimal sensor hydration, sensor noise, sensor drift and the like. In view of such issues, materials and methods designed to further the reliability of sensor readings are desirable.

SUMMARY OF THE INVENTION

Embodiments of the invention disclosed herein comprises sensor systems having architectures that include multiple in vivo probes and electrode arrays as well as algorithms designed for use with such systems. Such embodiments of the invention can be used to enhance sensor accuracy and reliability and overcome a number of technical challenges observed in this field. One illustrative embodiment is an amperometric analyte sensor system comprising a probe platform; a first probe coupled to the probe platform and adapted to be inserted in vivo, wherein the first probe comprises a first electrode array comprising a working electrode, a counter electrode and a reference electrode. Typically, the first probe also includes a second electrode array also comprising a working electrode, a counter electrode and a reference electrode. This system further includes a second probe that is also coupled to the probe platform and adapted to be inserted in vivo, the second probe including an electrode array comprising a working electrode, a counter electrode and a reference electrode. Typically, the second probe also includes an additional electrode array comprising a working electrode, a counter electrode and a reference electrode. In such systems, the electrode arrays are configured to be electronically independent from one another. As noted below, such systems can further include additional components that, for example, are used to provide comparative analyses of the independent signals received from the multiple sensor electrode arrays that are disposed on the two probes.

In typical embodiments of the invention, the amperometric analyte sensor system comprises one or more elements designed to record, analyze and/or characterize the independent signals received from the electrode arrays. For example, certain embodiments of the invention include a processor; a computer-readable program code having instructions, which when executed cause the processor to evaluate the independent signal data received from each of the first, second, third and fourth electrode arrays by comparing this data with one or more internal reliability parameters (e.g. a predetermined internal parameter such as one relating to signal amplitude); to rank signal data in accordance with this evaluation; and to then compute an analyte concentration using the ranked signal data from the electronically independent multiple electrode arrays. Embodiments of the invention typically include a number of additional components commonly used with analyte sensor systems, such as electrical conduits in operable contact with the various elements of the system, monitors adapted to display signal information, memory elements for storing signal data, power sources adapted to be coupled to the electrode arrays and the like.

In embodiments of the invention that evaluate a signal derived from an electrode array against one or more reliability parameters, a reliability parameter can be calculated by a method comprising for example: determining whether a signal amplitude one or more electrode arrays falls within a predetermined range of amplitudes; and/or determining a trend in sensor signals from a plurality of signals sensed by one or more electrode arrays; and/or determining an amount of nonspecific signal noise sensed by one or more electrode array; and/or determining a mean value for signals obtained from the first, second, third and fourth electrode arrays; and/or determining a standard deviation for signals obtained from the first, second, third or fourth electrode arrays. In certain embodiments of the invention, signal data from each of the first, second, third and fourth electrode arrays is weighted according to one or more reliability parameters; and the weighted signal data is computationally fused to determine an analyte concentration. In some embodiments of the invention, the processor further calculates a reliability index, wherein the reliability index provides an estimation of the reliability of the analyte concentration computed by the system. Optionally, signal data from each of the first, second, third and fourth electrode arrays is assessed so as to provide an indication of: the status of one or more of the first, second, third and fourth electrode arrays; and/or the status of the amperometric analyte sensor system comprising the first, second, third and fourth electrode arrays.

In embodiments of the invention, one or more electrodes in the first electrode array, the second electrode array, the third electrode array and/or the fourth electrode array are typically coated with a plurality of layered materials comprising an interference rejection layer; an analyte sensing layer; a protein layer; an analyte modulating layer disposed on the analyte sensing layer or the protein layer, wherein the analyte modulating layer comprises a composition that modulates the diffusion of an analyte diffusing through the analyte modulating layer; and an adhesion promoting layer disposed between the analyte modulating layer and the analyte sensing layer or the protein layer. Optionally, the interference rejection layer comprises crosslinked primary amine polymers or crosslinked methacrylate polymers. In certain embodiments of the invention, the crosslinked methacrylate polymers comprise Poly(2-hydroxyethyl methacrylate) polymers having an average molecular weight between 100 and 1000 kilodaltons. In certain embodiments of the invention, the analyte modulating layer comprises a blended mixture of a linear polyurethane/polyurea polymer, and a branched acrylate polymer that are blended together at a ratio of between 1:1 and 1:20 by weight %. In one illustrative embodiment, the analyte modulating layer comprises a polyurethane/polyurea polymer formed from a mixture comprising a diisocyanate; a hydrophilic polymer comprising a hydrophilic diol or hydrophilic diamine; and a siloxane having an amino, hydroxyl or carboxylic acid functional group at a terminus that is blended together in a 1:1 to 1:2 ratio with a branched acrylate polymer formed from a mixture comprising a butyl, propyl, ethyl or methyl-acrylate; an amino-acrylate; and a siloxane-acrylate; and a poly(ethylene oxide)-acrylate.

In some embodiments of the invention, electrodes in one or more of the arrays are constructed to have equivalent structural and/or material properties that allow them to have equivalent sensing functionalities. In other embodiments of the invention, electrodes in one or more of the arrays are constructed to have different structural and/or material properties that allow them to have different sensing functionalities. For example, in some embodiments of the invention, electrodes in the first electrode array and the third electrode array comprise a material (e.g. platinum black) having a first set of material properties; and/or are coated with a first set of layered materials and electrodes in the second electrode array and the fourth electrode array comprise a material having a second set of material properties; and/or are coated with a second set of layered materials. In certain illustrative embodiments of the invention, the size of the electroactive surface of the working electrodes differs. For example, in certain embodiments of the invention, working electrodes in the first and third electrode arrays are at least 1.5, 2 or 2.5 fold larger that the size of working electrodes in the second and fourth electrode arrays.

Embodiments of the invention are designed to address certain physiological and/or functional parameter phenomena that can influence sensor systems such as those that are adapted to sense glucose concentrations in a hospitalized diabetic patient. For example, in some embodiments of the invention, at least one electrode array is constructed from materials designed to predominantly sense signals resulting from the presence of glucose; and at least one electrode array is constructed from materials designed to predominantly sense signals resulting from background noise and/or signals resulting from interfering compounds. In other embodiments of the invention, at least one electrode array is constructed from materials designed to predominantly sense glucose at a concentration range of 40-100 mg/dL; and at least one electrode array is constructed from materials designed to predominantly sense glucose at a concentration range of 70-400 mg/dL.

Embodiments of the invention are further designed to address certain general phenomena observed in sensor systems. For example, in some embodiments of the invention, the processor evaluates signal data obtained from the electronically independent electrode arrays so as to provide evidence of signal drift over time in the amperometric analyte sensor system. In certain embodiments of the invention, the processor evaluates signal data so as to provide information on the initialization status of the amperometric analyte sensor system (e.g. data resulting from a plurality of amplitude pulses applied to the system). In such contexts, embodiments of the invention include using the analyte sensor system disclosed herein in methods designed to characterize the concentration of an analyte in an in vivo environment (e.g. glucose in a diabetic patient) and/or in methods designed to characterize the presence or levels of an interfering compound in an in vivo environment (e.g. acetaminophen, ascorbic acid etc.) and/or in methods of observing sensor signal drift (e.g. so as to observe sensor signal drift up or down over the in vivo lifetime of the sensor), and/or in methods of obtaining information on sensor start-up and initialization (e.g. to confirm that the sensor is ready to begin providing and/or characterizing information relating to blood glucose concentrations in a diabetic patient). Typically these systems use elements such as processors that obtain this information via comparative analyses of the independent signals received from the multiple sensor electrode arrays that are disposed on the two probes.

Embodiments of the invention further include using the disclosed sensor architectures and/or sensor algorithms in methods for sensing analytes in vivo (e.g. glucose concentrations in a diabetic patient). Typically, the method comprises observing signal data generated by a first, second, third and fourth electrode arrays in the presence of analyte, and then using this observed signal data to compute an analyte concentration. Such methods can include, for example, comparing signal data from each of the first, second, third and fourth electrode arrays and observing whether a signal obtained from each of the first, second, third and fourth electrode arrays falls within a predetermined range of values; and/or observing a trend in sensor signal data from each of the first, second, third and fourth electrode arrays; and/or observing an amount of nonspecific signal noise in each of the first, second, third and fourth electrode arrays. Typically in these methods, a comparison of the signal data obtained from the different arrays of is used to identify a signal from an array that is indicative of increasing glucose blood concentrations or decreasing blood glucose concentrations in the diabetic patient; and/or a signal that is indicative of insufficient sensor hydration; and/or a signal that is indicative of sensor signal drift; and/or a signal that is indicative of sensor loss of sensitivity to analyte (e.g. due to sensor component degradation). In certain embodiments the methods comprise assigning a weighted value to signal data obtained from each of the first, second, third and fourth electrode arrays; and using the weighted signal values to compute an analyte concentration by fusing the various weighted signal values.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE FIGURES

FIG. 3 shows an illustrative embodiment of a sensor assembly. The top panel provides a general view of illustrative internal elements of the assembly. The lower panel shows a cross section view of illustrative elements of the assembly.

DETAILED DESCRIPTION OF THE EMBODIMENTS

Figure 1:
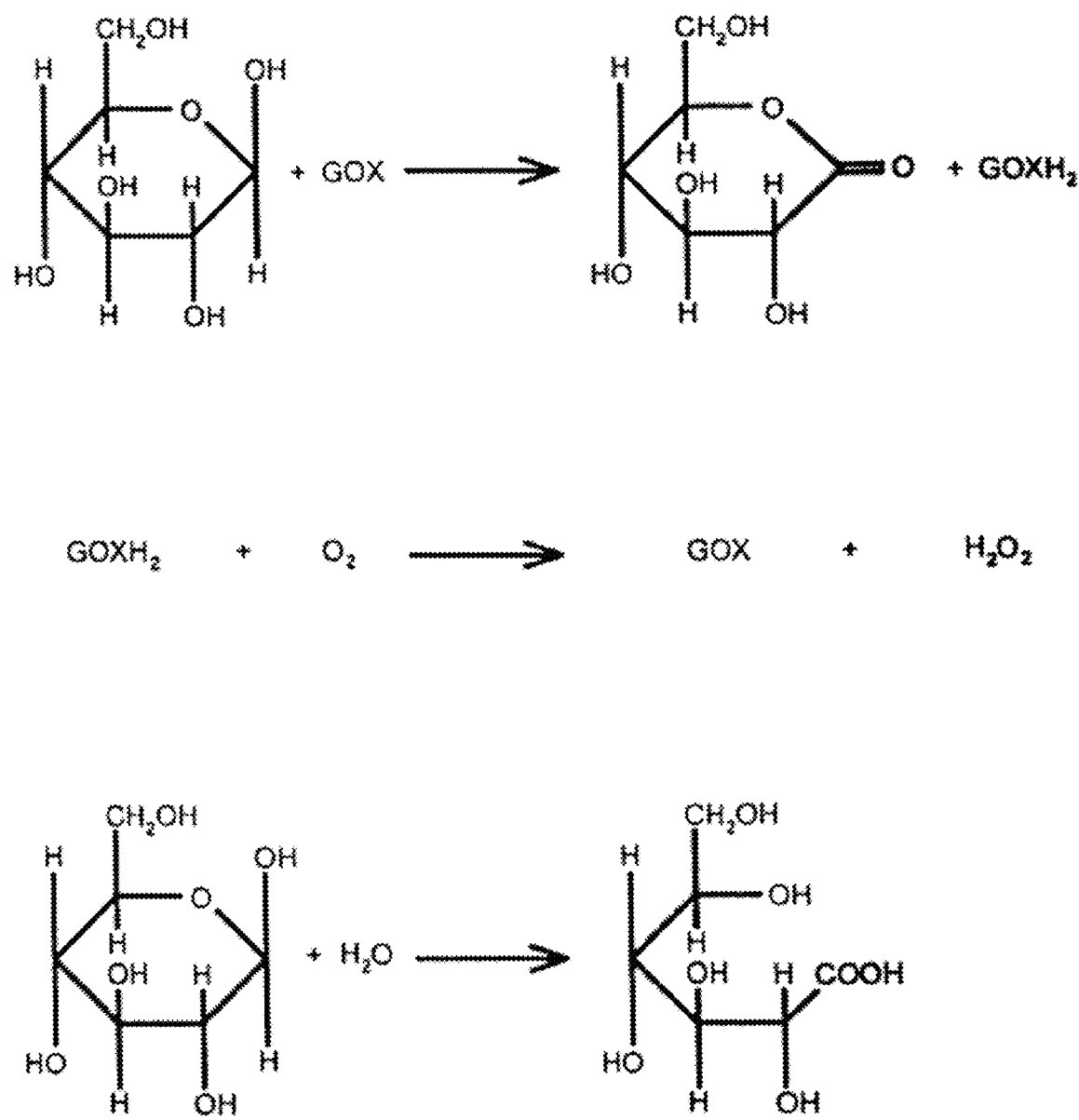
FIG. 1 provides a schematic of the well known reaction between glucose and glucose oxidase. As shown in a stepwise manner, this reaction involves glucose oxidase (GOx), glucose and oxygen in water. In the reductive half of the reaction, two protons and electrons are transferred from β-D-glucose to the enzyme yielding d-gluconolactone. In the oxidative half of the reaction, the enzyme is oxidized by molecular oxygen yielding hydrogen peroxide. The d-gluconolactone then reacts with water to hydrolyze the lactone ring and produce gluconic acid. In certain electrochemical sensors of the invention, the hydrogen peroxide produced by this reaction is oxidized at the working electrode ($H_2O_2 \rightarrow 2H^+ + O_2 + 2e^-$).

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. A number of terms are defined below. All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

It must be noted that as used herein and in the appended claims, the singular forms "a", "and", and "the" include plural referents unless the context clearly dictates otherwise. Thus, for example, reference to "an oxidoreductase" includes a plurality of such oxidoreductases and equivalents thereof known to those skilled in the art, and so forth. All numbers recited in the specification and associated claims that refer to values that can be numerically characterized with a value other than a whole number (e.g. the concentration of a compound in a solution) are understood to be modified by the term "about".

The term "oxidoreductase" is used according to its art accepted meaning, i.e. an enzyme that catalyzes the transfer of electrons from one molecule (the reductant, also called the hydrogen or electron donor) to another (the oxidant, also called the hydrogen or electron acceptor). Typical oxidoreductases include glucose oxidase and lactate oxidase. The term "carrier polypeptide" or "carrier protein" is used according to its art accepted meaning of an additive included to maintain the stability of a polypeptide, for example the ability of an oxidoreductase polypeptide to maintain certain qualitative features such as physical and chemical properties (e.g. an ability to oxidize glucose) of a composition comprising a polypeptide for a period of time. A typical carrier protein commonly used in the art is albumin.

The term "analyte" as used herein is a broad term and is used in its ordinary sense, including, without limitation, to refer to a substance or chemical constituent in a fluid such as a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to, lactate. Salts, sugars, proteins fats, vitamins and hormones naturally occurring in blood or interstitial fluids can constitute analytes in certain embodiments. The analyte can be naturally present in the biological fluid or endogenous; for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin. The metabolic products of drugs and pharmaceutical compositions are also contemplated analytes.

The terms "interferents" and "interfering species/compounds" are used in their ordinary sense, including, but not limited to, effects and/or chemical species/compounds that interfere with the measurement of an analyte of interest in a sensor to produce a signal that does not accurately represent the analyte measurement. In one example of an electrochemical sensor, interfering species are compounds with an oxidation potential that overlaps with the analyte to be measured so as to produce spurious signals.

The terms "electrochemically reactive surface" and "electroactive surface" as used herein are broad terms and are used in their ordinary sense, including, without limitation, the surface of an electrode where an electrochemical reaction takes place. In one example, a working electrode (e.g. one comprised of platinum black) measures hydrogen peroxide produced by the enzyme catalyzed reaction of the analyte being detected reacts creating an electric current (for example, detection of glucose analyte utilizing glucose oxidase produces $H_2O_2$ as a byproduct, $H_2O_2$ reacts with the surface of the working electrode producing two protons ($2H^+$), two electrons ($2e^-$) and one molecule of oxygen ($O_2$) which produces the electronic current being detected). In the case of the counter electrode, a reducible species, for example, $O_2$ is reduced at the electrode surface in order to balance the current being generated by the working electrode.

As discussed in detail below, embodiments of the invention relate to the use of an electrochemical sensor that exhibits a novel constellation of elements including sensor system architectures as well as algorithms for use with such sensors, constellations of elements that provide a unique set of technically desirable properties. The electrochemical sensors of the invention are designed to measure a concentration of an analyte of interest (e.g. glucose) or a substance indicative of the concentration or presence of the analyte in fluid. In some embodiments, the sensor is a continuous device, for example a subcutaneous, transdermal, or intravascular device. In some embodiments, the device can analyze a plurality of intermittent blood samples. Typically, the sensor is of the type that senses a product or reactant of an enzymatic reaction between an analyte and an enzyme in the presence of oxygen as a measure of the analyte in vivo or in vitro. Such sensors typically comprise a membrane surrounding the enzyme through which an analyte migrates. The product is then measured using electrochemical methods and thus the output of an electrode system functions as a measure of the analyte.

Embodiments of the invention disclosed herein provide sensors of the type used, for example, in subcutaneous or transcutaneous monitoring of blood glucose levels in a diabetic patient. A variety of implantable, electrochemical biosensors have been developed for the treatment of diabetes and other life-threatening diseases. Many existing sensor designs use some form of immobilized enzyme to achieve their biospecificity. Embodiments of the invention described herein can be adapted and implemented with a wide variety of known electrochemical sensors, including for example, U.S. Patent Application No. 20050115832, U.S. Pat. Nos. 6,001, 067, 6,702,857, 6,212,416, 6,119,028, 6,400,974, 6,595,919, 6,141,573, 6,122,536, 6,512,939 5,605,152, 4,431,004, 4,703,756, 6,514,718, 5,985,129, 5,390,691, 5,391,250, 5,482,473, 5,299,571, 5,568,806, 5,494,562, 6,120,676, 6,542,765 as well as PCT International Publication Numbers WO 01/58348, WO 04/021877, WO 03/034902, WO 03/035117, WO 03/035891, WO 03/023388, WO 03/022128, WO 03/022352, WO 03/023708, WO 03/036255, WO03/036310 WO 08/042,625, and WO 03/074107, and European Patent Application EP 1153571, the contents of each of which are incorporated herein by reference.

As discussed in detail below, embodiments of the invention disclosed herein provide sensor elements having enhanced material properties and/or architectural configurations and sensor systems constructed to include such elements (e.g. those comprising multiple electrode arrays disposed on multiple in vivo probes and associated software and electronic components such as a monitor, a processor and the like). The disclosure further provides methods for making and using such sensors and/or architectural configurations. While some embodiments of the invention pertain to glucose and/or lactate sensors, a variety of the elements disclosed herein (e.g. the algorithms) can be adapted for use with any one of the wide variety of sensors known in the art. The analyte sensor elements, architectures and methods for making and using these elements that are disclosed herein can be used to establish a variety of layered sensor structures. Such sensors of the invention exhibit a surprising degree of flexibility and versatility, characteristics which allow a wide variety of sensor configurations to be designed to examine a wide variety of analyte species.

Specific aspects of embodiments of the invention are discussed in detail in the following sections.

I. Typical Elements, Configurations and Analyte Sensor Embodiments of the Invention A wide variety of sensors and sensor elements are known in the art including amperometric sensors used to detect and/or measure biological analytes such as glucose. Many glucose sensors are based on an oxygen (Clark-type) amperometric transducer (see, e.g. Yang et al., Electroanalysis 1997, 9, No. 16: 1252-1256; Clark et al., Ann. N.Y. Acad. Sci. 1962, 102, 29; Updike et al., Nature 1967, 214,986; and Wilkins et al., Med. Engin. Physics, 1996, 18, 273.3-51). A number of in vivo glucose sensors utilize hydrogen peroxide-based amperometric transducers because such transducers are relatively easy to fabricate and can readily be miniaturized using conventional technology. Problems associated with the use of hydrogen peroxide-based amperometric transducers, however, include signal drift and signal interference due to electroactive substances present in the analyte environment. As discussed in detail below, these and other problems are addressed by using embodiments of the invention that are disclosed herein.

The invention disclosed herein has a number of embodiments. One illustrative embodiment is an amperometric analyte sensor system comprising: a probe platform; a first probe coupled to the probe platform and adapted to be inserted in vivo (e.g. is made from a biocompatible materials, has a relatively smooth surface and an architecture designed to avoid unnecessary tissue damage upon insertion etc.), wherein the first probe comprises a first electrode array comprising a working electrode, a counter electrode and a reference electrode. Typically the first probe includes another electronically independent electrode array also comprising a working electrode, a counter electrode and a reference electrode. This system further includes a second probe that is also coupled to the probe platform and adapted to be inserted in vivo, the second probe including another electronically independent electrode array comprising a working electrode, a counter electrode and a reference electrode. Typically this second probe includes another electronically independent electrode array comprising a working electrode, a counter electrode and a reference electrode. In certain embodiments of the invention, the first or second probe contain 3, 4, 5, 6 or more electronically independent electrode arrays, each comprising a working electrode, a counter electrode and a reference electrode. Other embodiments of the invention can include 3, 4, 5 or more in vivo probes on which the independent electrode arrays are disposed.

Figure 4:
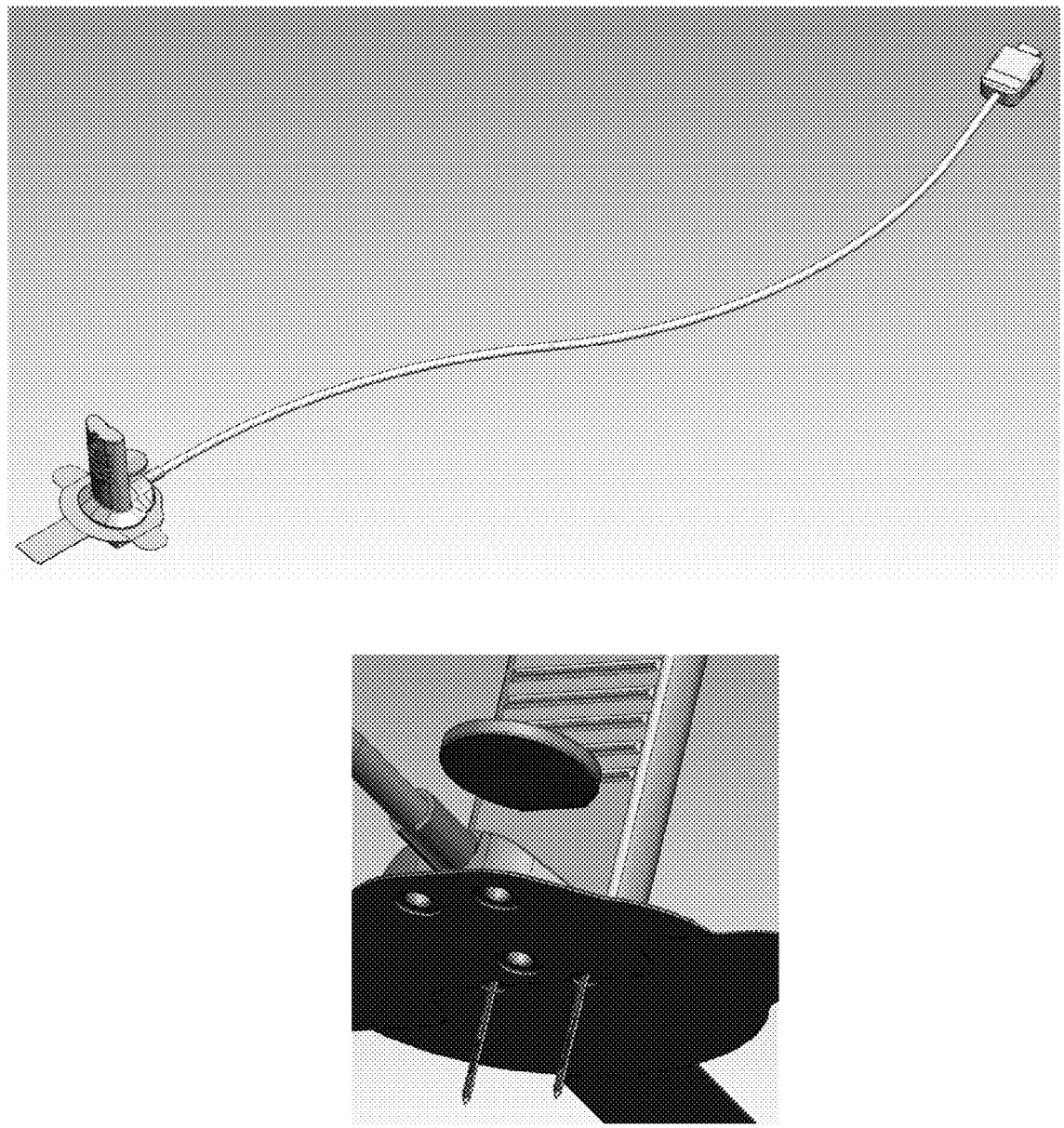
FIG. 4 shows an illustrative embodiment of a sensor assembly. The top panel provides a general view of a needle hub assembly, a sensor and a cable assembly. The lower panel shows a close up view of a dual probe sensor with two needles.
Figure 5:
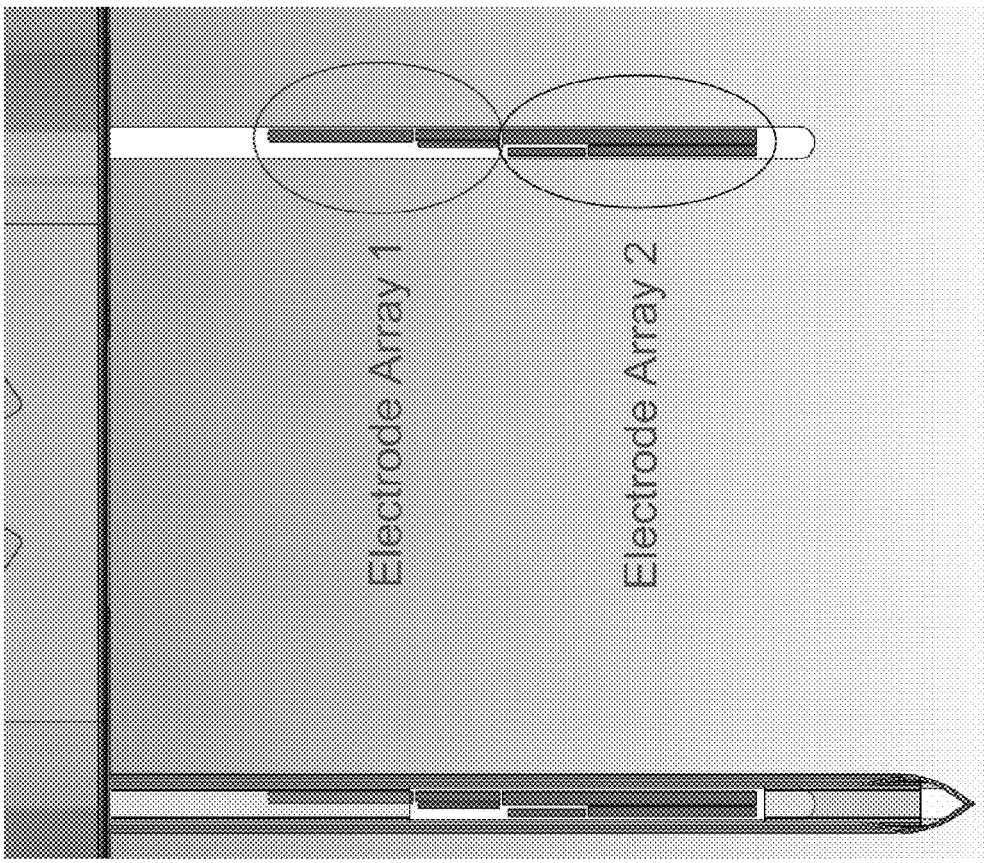
FIG. 5 shows an illustrative embodiment of a sensor probe arrangement. In this embodiment, each sensor probe has 2 electrode arrays. In this embodiment, each electrode array is a 3 electrode system with working, counter, reference electrode so that the assembly is 4 electrode arrays as there are 2 sensor probes. In this embodiment, the 4 independent glucose sensor signals allows for improved system reliability and accuracy, factors which can be further enhanced for example through the use of certain algorithms disclosed herein.

In certain embodiments of the invention, the probes comprising the electrode arrays are releasably coupleable with the probe platform (e.g. can be engaged to and disengaged from the probe platform). In some embodiments, the probe platform is used to facilitate insertion of the in vivo probes, and the probes are released from the probe platform following their insertion in vivo. In other embodiments, the probe platform is used to facilitate insertion and stabilization of the in vivo probes, and the probes remain coupled to the probe platform following their insertion in vivo. In such systems, the electrode arrays are typically configured to be electronically interrogated independently of one another. In illustrative embodiments of the invention, the electrode arrays are configured to be electronically independent of each other by having independent electrical conduits connected to each electrode array comprising a working, counter and reference electrode, wherein the independent electrical conduits are then independently coupled to the element(s) in the system that are designed to send or receive such signals or store signal data (e.g. a processor or the like). One illustrative specific embodiment of the invention is a hospital sensor system that can be used to monitor the blood glucose a patient (e.g. a diabetic patient); this sensor comprises a total of four independent glucose sensor arrays. Illustrative architectural configurations for such sensor systems are shown in FIGS. 3-5. Illustrative algorithms useful with these sensor systems are discussed below as well as in U.S. application Ser. No. 12/914,969, filed Oct. 28, 2011 (see, e.g. paragraphs [0056]-[0125]), the contents of which are incorporated herein by reference.

As noted above, certain embodiments of the invention combine sensor architectures disclosed herein with a processor to use combined or fused sensor signals to, for example, assess the reliability of a glucose sensor system. Such systems can, for example, monitor the sensor signals from multiple electrode arrays and then convert sensor signals to glucose value as well as provide information on the reliability of this signal information. In this way, the sensor systems disclosed herein can overcome a number of problems with sensor accuracy and reliability that are observed in this technology. In particular, as is known in the art, electrochemical analyte sensors can experience problems due to both the in vivo environment in which they are disposed as well as the functional degradation of the sensor components themselves. For example, the reliability of electrode array signals can be questionable in situations where the electrode array is inadvertently disposed in vivo at a site having suboptimal tissue properties (e.g. scar tissue) and/or is disposed at a suboptimal tissue depth (which can, for example, result in suboptimal hydration of the sensor). Moreover, the reliability of electrode array signals can also be questionable in situations where the sensor output signal slowly changes independent of the measured property, a phenomena termed drift. Sensor drift usually indicates a slow degradation of sensor properties over a period of time. In addition, for reasons that are not always understood, sensors can experience different levels of noise (a random deviation of the signal that varies in time). Unfortunately it is often difficult to differentiate between the signals that are generated/altered by such phenomena and true signals that reflect levels of analyte to be measured.

Embodiments of the invention provide a sensor architecture having specific constellations of elements designed to address the above-noted problems. For example, embodiments of the invention are designed so that their multiple electrode arrays, which comprise a working, counter and reference electrode, are configured to be electronically independent (e.g. are individually and separately wired). This electronic independence ensures that each sensing array is not influenced by any other array, thereby ensuring that the signals obtained from each array represent isolated characterizations of, for example, the in vivo environment in which the array is disposed. Embodiments include sensor systems comprising two probes disposed on a shared platform, each probe having two electrode arrays. Such sensor systems provide a device that easily inserts multiple electrode sensing arrays in two proximal in vivo environments, thereby allowing one to determine and/or characterize confounding sensor readings that result from factors specific to the environment in which the array is disposed. Similarly, by including at least two arrays on each probe, one can further determine and/or characterize confounding sensor readings that relate to problems with a single array on that probe, for example a single array that is inadequately hydrated as well as a single array that is degrading and exhibiting loss of function. Issues with hydration and/or sensor environment and/or other factors relating to the depth at which an array is inserted are further addressed by embodiments of the invention where a first and second electrode array on a probe are disposed at different locations along the probe so that the first and second electrode arrays are located at different depths when inserted into an in vivo environment. In some embodiments of the invention, the system further comprises an adhesive patch adapted to secure the probe platform to the skin of a patient (e.g. to facilitate anchoring the arrays in vivo and inhibit their movement).

In addition, sensor systems having architectures with two probes, each having at least two electrode arrays disposed therein, are designed to be coupled with specialized sensor algorithms adapted for use with the disclosed sensor architectures (e.g. processes which further their ability generate highly reliable sensor readings). For example, the sensor algorithms can compare the signals received from each array to each other (e.g. to determine if a signal obtained from an array is one or more standard deviations away from the signals obtained from the other arrays) and/or to one or more internal reference standards (e.g. a range in which valid signals will fall) in order to identify an array that may be providing a suboptimal signal due to, for example, being disposed in a suboptimal environment, poor hydration, general degradation and the like. These sensor algorithms can further assign a weight to each sensor signal based upon this comparison (e.g. electrode arrays identified as generating questionable signals (e.g. a mean or median single sensor array signal that is at least 10%, 20%, 30%, 40%, 50% or more off from the signals obtained from the other sensor arrays) or given lower weight (or no weight) as compared to the electrode arrays in the system that exhibit signals that, for example, fall within an expected range and/or are consistent with the signals obtained from the other electrode arrays in the sensor system). In this way, these weighted signals can then be "fused" to generate a single output representative of the analyte concentration. As illustrated in Example 4, glucose monitoring systems having this constellation of elements exhibit enhanced performance in the critically ill. In addition, the sensor algorithms are further designed to include signal integrity checks by, for example, generating a reliability index which allows a user to simultaneously gauge the reliability of each reading. In this way, these sensor embodiments can address a number of problems with sensor accuracy and reliability that are observed in this technology. Further aspects of such algorithms are discussed below.

As noted above, illustrative functionalities of the sensor systems disclosed herein include signal integrity checks. For example such systems can calculate internal reliability indexes (IRIs) and/or calculate and output a reliability index (RI) indicating sensor glucose (SG) reliability and/or calculate and output quad sensor status (QSS) for system control logic. Such systems can include calibration steps which, for example, convert each sensor signal to sensor glucose (SG) based on input blood glucose (BG). Typically such systems include a sensor fusion function that examines (and optionally assigns a weight to) factors such as sensor glucose signals from each electronically independent electrode array in and then "fuses" multiple signals to generate and output a single sensor glucose and/or reliability index (e.g. a reliability index for a single electrode array within the system and/or a comprehensive reliability index for the whole system). Illustrative SG outputs can include, for example, sensor glucose (e.g. in a concentration range of 40~400 mg/dL) that are calculated every minute. Illustrative reliability outputs measure how reliable the sensor signal and can, for example be formatted in a numerical range of 0~1 and calculated every minute to provide four possible status indicators: pending (e.g. in sensor initialization and stabilization), good, bad, and failed. Artisans can use such system parameters to, for example detect sensor trends including a long-term, non-physiological trend, and/or a sensor failure as well as to characterize the noise of Isig in real-time.

In embodiments of the invention that evaluate a signal derived from an electrode array against one or more reliability parameters, a reliability parameter can be calculated by a method comprising for example: determining whether a signal amplitude one or more electrode arrays falls within a predetermined range of amplitudes; and/or determining a trend in sensor signals from a plurality of signals sensed by one or more electrode arrays (e.g. so as to observe sensor signal drift in one or more arrays); and/or determining an amount of nonspecific signal noise sensed by one or more electrode arrays (e.g. in order to compare this signal to one or more predetermined internal noise parameters); and/or determining a mean value for signals obtained from the first, second, third and fourth electrode arrays (e.g. in order to compare this value to predetermined internal mean parameters); and/or determining a standard deviation for signals obtained from the first, second, third or fourth electrode arrays (e.g. in order to compare these values to predetermined internal standard deviation parameters). In typical embodiments of the invention, signal data recorded from each of the first, second, third and fourth electrode arrays is weighted according to one or more reliability parameters; and the weighted signal data is computationally fused to determine an analyte concentration. Optionally, signal data recorded from each of the first, second, third and fourth electrode arrays is assessed so as to provide an indication of: the status of one or more of the first, second, third and fourth electrode arrays; and/or the status of the amperometric analyte sensor system comprising the first, second, third and fourth electrode arrays.

In certain embodiments of the invention, the electrode arrays are coupled to flex assemblies in order to avoid problems that can occur with implantable sensors and sensor systems due to lack of hydration (e.g. slow start-up initialization times) and/or fluid stagnation by enhancing the flexing and movement of the implanted components in a manner that enhances fluid flow around these components and inhibits the likelihood of a gas bubble and/or a stagnating pool of fluid and/or biofouling macromolecules from forming and/or remaining on top of or close to an electrode in a manner that compromises sensor function. In addition, embodiments of the invention that comprise flex assemblies can be combined with certain complementary elements disclosed herein so as to further overcome problems that result from a lack of hydration, gas bubble formation, fluid stagnation, biofouling, a patient's immune response, or the like (e.g. distributed electrode configurations, multiple electrode sensors, multiple sensor apparatuses having multiple implantation sites, voltage pulsing methods etc.).

Typical electrode arrays comprise a plurality of working electrodes, counter electrodes and reference electrodes. Optionally, the plurality of working, counter and reference electrodes are grouped together as a unit and positionally distributed on the conductive layer in a repeating pattern of units. Alternatively, the plurality of working, counter and reference electrodes are grouped together and positionally distributed on the conductive layer in a non-repeating pattern of units. In certain embodiments of the invention, the elongated base layer is made from a material that allows the sensor to twist and bend when implanted in vivo; and the electrodes are grouped in a configuration that facilitates an in vivo fluid to contact at least one of the working electrode as the sensor apparatus twists and bends when implanted in vivo. In some embodiments, the electrodes are grouped in a configuration that allows the sensor to continue to maintain optimal functionality if a portion of the sensor having one or more electrodes is dislodged from an in vivo environment and exposed to an ex vivo environment.

In one embodiment of the sensor having a distributed electrode configuration designed to facilitate hydration, the working electrode, the counter electrode and the reference electrode are positionally distributed on a conductive layer in a configuration arranged so that a first electrode is disposed in a region on a first edge of the elongated base layer; a second electrode is disposed in a region on an opposite edge of the elongated base layer; and a third is disposed in a region of the elongated base layer that is between the first electrode and the second electrode. Optionally, the working electrode, the counter electrode and the reference electrode are positionally distributed on a conductive layer in a configuration arranged so that the working electrode is disposed in a region on a first edge of the elongated base layer; the counter electrode is disposed in a region on an opposite edge of the elongated base layer; and the reference electrode is disposed in a region of the elongated base layer that is between the working electrode and the counter electrode. In some embodiments of the invention, the reference electrode is at the proximal end of an implanted sensor (i.e. closest to the skin surface). In other embodiments, the reference electrode is at the distal end of an implanted sensor.

Typically, the electrodes in a sensor are of a rectangular shape, i.e. having a longer side and a shorter side (including those of a rectangular shape, yet having rounded edges). In some embodiments of the invention, the electrode configuration is such that a longer side of at least one of the electrodes in a distributed electrode pattern is parallel to a longer side of at least one of the other electrodes in the distributed electrode pattern (and optionally all of the electrodes in the distributed electrode pattern). As shown in FIGS. 6B and 6C of U.S.

patent application Ser. No. 12/184,046, the contents of which are incorporated herein by reference, sensor embodiments having such configurations are observed to exhibit a better start-up profile than sensors without electrodes configured in this pattern. In certain embodiments of the invention, an edge or center of a side of a reference electrode is lined up with an edge or center of a side of the working or counter electrode. Typically in these embodiments the sides are the longer sides of a rectangular electrode. In some embodiments of the invention, an edge or center of a side of a reference electrode is offset about 25 or 50% with an edge or center of a side of a working or counter electrode. In some embodiments of the invention, the reference electrode is formed in the sensor so as to have a side wall architecture that does not inhibit fluid flow (or no side-walls) so as to improve hydration of the sensor upon contact with a fluid sample. Related embodiments of the invention include methods for using a distributed electrode configuration to facilitate the hydration and/or initialization of various sensor embodiments of the invention.

In embodiments of the invention, one or more electrodes in a first electrode array, a second electrode array, a third electrode array or a fourth electrode array are typically coated with a plurality of layered materials comprising, for example one or more of an interference rejection layer; an analyte sensing layer; a protein layer; an analyte modulating layer disposed on the analyte sensing layer or the protein layer, wherein the analyte modulating layer comprises a composition that modulates the diffusion of an analyte diffusing through the analyte modulating layer; and an adhesion promoting layer disposed between the analyte modulating layer and the analyte sensing layer or the protein layer. Illustrative non-limiting embodiments of such layered structures are shown for example in FIGS. 2A-2C. A wide variety of materials can be used to form such layers of the sensor. Optionally for example, the interference rejection layer comprises crosslinked primary amine polymers or crosslinked methacrylate polymers. In certain embodiments of the invention, the crosslinked methacrylate polymers comprise Poly(2-hydroxyethyl methacrylate) polymers having an average molecular weight between 100 and 1000 kilodaltons. In certain embodiments of the invention, an interference rejection membrane (IRM) is characterized as having a specific response to an interfering compound, for example a sensor with one type of IRM has a 50% response (or has greater than or less than a 50% response) to 20 mg/dL acetaminophen.

In embodiments of the invention, the analyte modulating layer can comprise a blended mixture of a linear polyurethane/polyurea polymer, and a branched acrylate polymer that are blended together at a ratio of between 1:1 and 1:20 by weight %. In one illustrative embodiment, the analyte modulating layer comprises a polyurethane/polyurea polymer formed from a mixture comprising a diisocyanate; a hydrophilic polymer comprising a hydrophilic diol or hydrophilic diamine; and a siloxane having an amino, hydroxyl or carboxylic acid functional group at a terminus that is blended together in a 1:1 to 1:2 (e.g. 1:1.5) ratio with a branched acrylate polymer formed from a mixture comprising a butyl, propyl, ethyl or methyl-acrylate; an amino-acrylate; and a siloxane-acrylate; and a poly(ethylene oxide)-acrylate.

In certain embodiments of the invention, the sensor is a glucose oxidase based glucose sensor and the analyte modulating layer is a glucose limiting membrane (GLM) layer that comprises a linear polyurethane/polyurea polymer blended with a branched acrylate polymer at a ratio of 1:1 to 1:2. The blending of these polymers allows for the modulation of glucose diffusion to the electrode and can be advantageous in certain situations. For example, using a pure branched acrylate polymer may result in the saturation of glucose to the electrode as the permeability of branched acrylate polymer is very large compared to a linear polyurethane/polyurea polymer. Excessive glucose diffusion to the electrode in in-vivo studies can cause an unstable sensor signal as the sensor may be limited by low oxygen concentrations. By blending a linear polyurethane/polyurea polymer with branched acrylate polymer, a higher signal sensor can be produced while preventing glucose saturation (relative to the co-reactant oxygen) from occurring. A high signal sensor benefits from a larger signal to noise ratio and provides improved sensor accuracy in the hypoglycemic region, a property which can be critical for patients in the hospital environment. In this context, certain embodiments of the invention comprise sensor arrays coated with different glucose limiting membranes (e.g. compositions having different rations of polymers).

In some embodiments of the invention, electrodes in one or more of the arrays are constructed to have equivalent (or identical) structural and/or material properties that allow them to have equivalent (or identical) sensing functionalities. In other embodiments of the invention, electrodes in one or more of the arrays are constructed to have different structural and/or material properties that allow them to have different sensing functionalities. For example, in some embodiments of the invention, electrodes in the first electrode array and the third electrode array comprise a material (e.g. a glucose limiting membrane) having a first set of material properties; and/or are coated with a first set of layered materials and electrodes in the second electrode array and the fourth electrode array comprise a material having a second set of material properties; and/or are coated with a second set of layered materials. For example, in one such embodiment of the invention, the platinum used to form electrodes of the different sensor arrays is plated under differing conditions for different arrays (e.g. a first electrode array comprises an electrode plated with platinum under a first set of plating conditions, and a second electrode array comprises an electrode plated with platinum under a second set of plating conditions). In addition, in certain illustrative embodiments of the invention, the size of the electroactive surface of the working electrodes differs. For example, in certain embodiments of the invention, working electrodes in the first and third electrode arrays are at least 1.5, 2 or 2.5 fold larger that the size of working electrodes in the second and fourth electrode arrays.

In certain embodiments of the invention, the amperometric analyte sensor system comprises one or more elements designed to record, analyze and/or characterize signals received from the electrode arrays. For example, certain embodiments of the invention include a processor; a computer-readable program code having instructions, which when executed causes the processor to assess signal data obtained from each of the first, second, third and fourth electrode arrays by comparing this data to one or more reliability parameters; to rank signal data obtained from each of the first, second, third and fourth electrode arrays in accordance with this assessment; and to then compute an analyte concentration using ranked signal data from each of the first, second, third and fourth electrode arrays. Embodiments of the invention also typically include a number of additional components commonly used with analyte sensor systems, such as electrical conduits in operable contact with the various electrical elements of the system, monitors adapted to display signal information and, power sources adapted to be coupled to the electrode arrays etc.

Certain embodiments of the invention are specifically adapted to sense glucose in vivo, for example in a diabetic patient. In some embodiments of the invention, the electrode arrays can be formed to have identical sensing capabilities, in order to, for example, provide a comparative signal that can be used to assess and take into account factors influencing sensor performance such as the tissue characteristics at the site of implantation, as well as to provide a comparative signal that can be used to assess the performance of each electrode array that is used to sense glucose (e.g. as a way to test and characterize individual electrode array as well as total sensor reliability). Alternatively, the electrode arrays can be formed to have different sensing capabilities. For example, in some embodiments of the invention, at least one electrode array is constructed from materials designed to predominantly sense glucose at a concentration range of 40-100 mg/dL; and at least one electrode array is constructed from materials designed to predominantly sense glucose at a concentration range of 70-400 mg/dL. Similarly, in some embodiments of the invention, at least one electrode array is constructed from materials designed to predominantly sense signals resulting from the presence of glucose; and at least one electrode array is constructed from materials designed to predominantly sense signals resulting from background noise and/or signals resulting from interfering compounds. Similarly, in some embodiments of the invention, multiple analytes are sensed. In some embodiments at least one electrode array is constructed from materials designed to predominantly sense signals resulting from the presence of a first analyte, for example glucose; and at least one electrode array is constructed from materials designed to predominantly sense signals resulting from a second analyte, for example lactate.

Embodiments of the invention are designed to address certain general phenomena observed in sensor systems. For example, in some embodiments of the invention, the processor evaluates data provided by each of the individual electrode arrays so as to provide evidence of signal drift over time in the amperometric analyte sensor system. In some embodiments of the invention, the processor evaluates data so as to provide information on the initialization status of the amperometric analyte sensor system (e.g. data resulting from a plurality of amplitude pulses applied to the system). In such contexts, embodiments of the invention include using the analyte sensor system disclosed herein in methods designed to characterize the concentration of an analyte in an in vivo environment (e.g. glucose in a diabetic patient) and/or in methods designed to characterize the presence or levels of an interfering compound in an in vivo environment (e.g. acetaminophen, ascorbic acid etc.) and/or in methods of observing sensor signal drift (e.g. so as to observe sensor signal drift up or down over the in vivo lifetime of the sensor), and/or in methods of obtaining information on sensor start-up and initialization (e.g. to confirm that the sensor is ready to begin providing and/or characterizing information relating to blood glucose concentrations in a diabetic patient).

In addition to the sensor structures discussed above, embodiments of the invention relate to using these specific sensor structures in methods, systems, apparatuses, and/or articles, etc. for glucose sensor signal reliability analysis. In this context, glucose monitoring systems, including ones that are designed to adjust the glucose levels of a patient and/or to operate continually (e.g., repeatedly, at regular intervals, at least substantially continuously, etc.), may comprise a glucose sensor signal that may be assessed for reliability. More specifically, but by way of example only, reliability assessment(s) on glucose sensor signals may include glucose sensor signal stability assessment(s) to detect an apparent change in responsiveness of a signal.

Embodiments of the invention further include using the disclosed sensor architectures and/or sensor algorithms in methods for sensing analytes in vivo (e.g. glucose concentrations in a diabetic patient). Typically, the method comprises observing signal data generated by a first, second, third and fourth electrode arrays in the presence of analyte, and then using this observed signal data to compute an analyte concentration. Such methods can include, for example, comparing signal data from each of the first, second, third and fourth electrode arrays and observing whether a signal obtained from each of the first, second, third and fourth electrode arrays falls within a predetermined range of values; and/or observing a trend in sensor signal data from each of the first, second, third and fourth electrode arrays; and/or observing an amount of nonspecific signal noise in each of the first, second, third and fourth electrode arrays. Typically in these methods, a comparison of the signal data obtained from the different arrays is used to identify a signal from an array that is indicative of increasing glucose blood concentrations or decreasing blood glucose concentrations in the diabetic patient; and/or a signal that is indicative of insufficient sensor hydration; and/or a signal that is indicative of sensor signal drift; and/or a signal that is indicative of sensor loss of sensitivity to analyte (e.g. due to sensor component degradation). In certain embodiments the methods comprise assigning a weighted value to signal data obtained from each of the first, second, third and fourth electrode arrays; and using the weighted signal values to compute an analyte concentration by fusing the various weighted signal values. Other embodiments of the invention include using the processor to: assess signal data from each of the first, second, third and fourth electrode array; and generate reliability index that indicates the reliability of a signal obtained from one or more of the first, second, third and fourth electrode arrays.

In embodiments of the invention, one or more electrodes in the first electrode array, the second electrode array, the third electrode array and the fourth electrode array are coated with a plurality of layered materials. The plurality of layered materials comprising: an interference rejection layer; an analyte sensing layer; a protein layer; an adhesion promoting layer; and an analyte modulating layer, wherein the analyte modulating layer comprises a composition that modulates the diffusion of an analyte diffusing through the analyte modulating layer.

The systems of the invention typically use the disclosed architectures in combination with methods/algorithms adapted for use with such architectures to provide sensors having a greater reliability than conventional sensor designs. In one or more example embodiments, a sensing method may include: obtaining a series of samples of at least one sensor signal that is responsive to a blood glucose level of a patient; determining, based at least partly on the series of samples, at least one metric assessing an underlying trend of a change in responsiveness of the at least one sensor signal to the blood glucose level of the patient over time; and assessing a reliability of the at least one sensor signal to respond to the blood glucose level of the patient based at least partly on the at least one metric assessing an underlying trend.

In some embodiments of the invention, a sensing methodology may include: generating an alert signal responsive to a comparison of the at least one metric assessing an underlying trend with at least one predetermined threshold. In at least one example implementation, the assessing may include comparing the at least one metric assessing an underlying trend with at least a first predetermined threshold and a second predetermined threshold. In at least one other example implementation, the assessing may further include: assessing that the reliability of the at least one sensor signal is in a first state responsive to a comparison of the at least one metric assessing an underlying trend with the first predetermined threshold; assessing that the reliability of the at least one sensor signal is in a second state responsive to a comparison of the at least one metric assessing an underlying trend with the first predetermined threshold and the second predetermined threshold; and assessing that the reliability of the at least one sensor signal is in a third state responsive to a comparison of the at least one metric assessing an underlying trend with the second predetermined threshold. In at least one other example implementation, the assessing may further include: ascertaining at least one value indicating a severity of divergence by the at least one sensor signal from the blood glucose level of the patient over time based at least partly on the at least one metric assessing an underlying trend, the first predetermined threshold, and the second predetermined threshold.

In other embodiments of the invention, a sensing methodology may include: acquiring the at least one sensor signal from one or more subcutaneous glucose sensors, wherein the at least one metric assessing an underlying trend may reflect an apparent reliability of the at least one sensor signal that is acquired from the one or more subcutaneous glucose sensors. In at least one example implementation, the method may further include: altering an insulin infusion treatment for the patient responsive at least partly to the assessed reliability of the at least one sensor signal.

In at least one example implementation, the determining may include: producing the at least one metric assessing an underlying trend using a slope of a linear regression that is derived at least partly from the series of samples of the at least one sensor signal. In at least one other example implementation, the method may include: transforming the series of samples of the at least one sensor signal to derive a monotonic curve, wherein the producing may include calculating the slope of the linear regression, with the linear regression being derived at least partly from the monotonic curve.

In at least one example implementation, the determining may include: decomposing the at least one sensor signal as represented by the series of samples using at least one empirical mode decomposition and one or more spline functions to remove relatively higher frequency components from the at least one sensor signal. In at least one example implementation, the determining may include: decomposing the at least one sensor signal as represented by the series of samples using at least one discrete wavelet transform; and reconstructing a smoothed signal from one or more approximation coefficients resulting from the at least one discrete wavelet transform. In at least one example implementation, the determining may include: iteratively updating a trend estimation at multiple samples of the series of samples of the at least one sensor signal based at least partly on a trend estimation at a previous sample and a growth term.

In one or more example embodiments, an apparatus may include: a controller to obtain a series of samples of at least one sensor signal that is responsive to a blood glucose level of a patient, and the controller may include one or more processors to: determine, based at least partly on the series of samples, at least one metric assessing an underlying trend of a change in responsiveness of the at least one sensor signal to the blood glucose level of the patient over time; and assess a reliability of the at least one sensor signal to respond to the blood glucose level of the patient based at least partly on the at least one metric assessing an underlying trend. In at least one example implementation, the one or more processors of the controller may further be to: generate an alert signal responsive to a comparison of the at least one metric assessing an underlying trend with at least one predetermined threshold.

In at least one example implementation, the controller may be capable of assessing by: comparing the at least one metric assessing an underlying trend with at least a first predetermined threshold and a second predetermined threshold. In at least one other example implementation, the controller may be further capable of assessing by: assessing that the reliability of the at least one sensor signal is in a first state responsive to a comparison of the at least one metric assessing an underlying trend with the first predetermined threshold; assessing that the reliability of the at least one sensor signal is in a second state responsive to a comparison of the at least one metric assessing an underlying trend with the first predetermined threshold and the second predetermined threshold; and assessing that the reliability of the at least one sensor signal is in a third state responsive to a comparison of the at least one metric assessing an underlying trend with the second predetermined threshold. In at least one other example implementation, the controller may be further capable of assessing by: ascertaining at least one value indicating a severity of divergence by the at least one sensor signal from the blood glucose level of the patient over time based at least partly on the at least one metric assessing an underlying trend, the first predetermined threshold, and the second predetermined threshold.

In at least one example implementation, the one or more processors of the controller may further be used to: acquire the at least one sensor signal from one or more subcutaneous glucose sensors, wherein the at least one metric assessing an underlying trend may reflect an apparent reliability of the at least one sensor signal that is acquired from the one or more subcutaneous glucose sensors. In at least one example implementation, the one or more processors of the controller may further be to: alter an insulin infusion treatment for the patient responsive at least partly to the assessed reliability of the at least one sensor signal.

In at least one example implementation, the controller may be capable of determining by: producing the at least one metric assessing an underlying trend using a slope of a linear regression that is derived at least partly from the series of samples of the at least one sensor signal. In at least one example implementation, the one or more processors of the controller may further be used to: transform the series of samples of the at least one sensor signal to derive a monotonic curve, wherein the controller may be capable of producing the at least one metric assessing an underlying trend by calculating the slope of the linear regression, with the linear regression being derived at least partly from the monotonic curve.

In at least one example implementation, the controller may be capable of determining by: decomposing the at least one sensor signal as represented by the series of samples using at least one empirical mode decomposition and one or more spline functions to remove relatively higher frequency components from the at least one sensor signal. In at least one example implementation, the controller may be capable of determining by: decomposing the at least one sensor signal as represented by the series of samples using at least one discrete wavelet transform; and reconstructing a smoothed signal from one or more approximation coefficients resulting from the at least one discrete wavelet transform. In at least one example implementation, the controller may be capable of determining by: iteratively updating a trend estimation at multiple samples of the series of samples of the at least one sensor signal based at least partly on a trend estimation at a previous sample and a growth term.

In one or more example embodiments, a system may include: means for obtaining a series of samples of at least one sensor signal that is responsive to a blood glucose level of a patient; means for determining, based at least partly on the series of samples, at least one metric assessing an underlying trend of a change in responsiveness of the at least one sensor signal to the blood glucose level of the patient over time; and means for assessing a reliability of the at least one sensor signal to respond to the blood glucose level of the patient based at least partly on the at least one metric assessing an underlying trend.

In one or more example embodiments, an article may include at least one storage medium having stored thereon instructions executable by one or more processors to: obtain a series of samples of at least one sensor signal that is responsive to a blood glucose level of a patient; determine, based at least partly on the series of samples, at least one metric assessing an underlying trend of a change in responsiveness of the at least one sensor signal to the blood glucose level of the patient over time; and assess a reliability of the at least one sensor signal to respond to the blood glucose level of the patient based at least partly on the at least one metric assessing an underlying trend.

Other exemplary embodiments are described herein and/or illustrated in the accompanying drawings. Additionally, particular example embodiments may be directed to an article comprising a storage medium including machine-readable instructions stored thereon which, if executed by a special purpose computing device and/or processor, may be directed to enable the special purpose computing device/processor to execute at least a portion of the described method(s) according to one or more particular implementations. In other particular example embodiments, a sensor may be adapted to generate one or more signals responsive to a measured blood glucose concentration in a body while a special purpose computing device and/or processor may be adapted to perform at least a portion of described method(s) according to one or more particular implementations based upon the one or more signals generated by the sensor.

Figure 7:
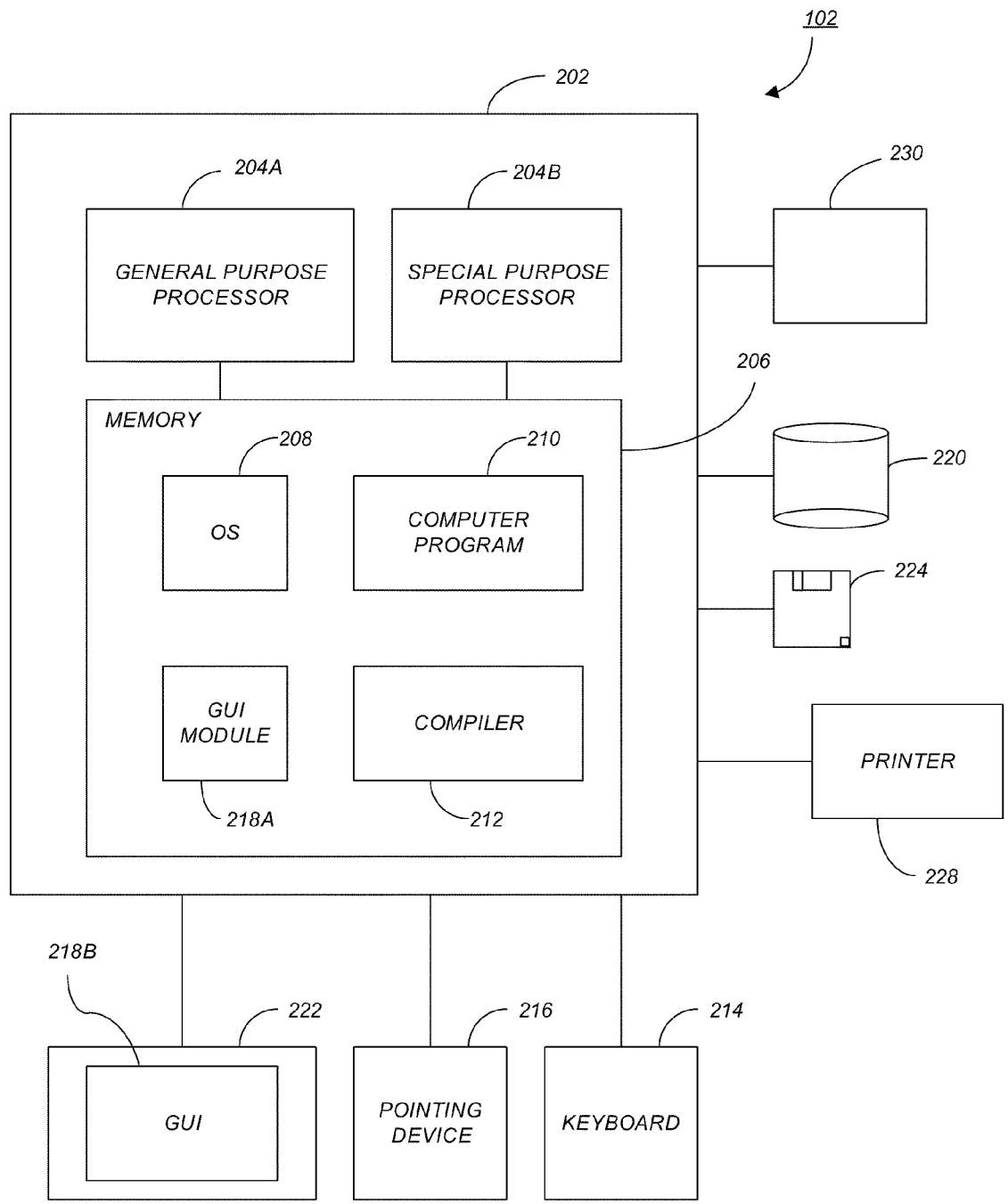
FIG. 7 presents an exemplary generalized computer system 202 that can be used to implement elements of the present invention.

Embodiments of the invention disclosed herein can be performed for example, using one of the many computer systems known in the art (e.g. those associated with medication infusion pumps). FIG. 7 illustrates an exemplary generalized computer system 202 that can be used to implement elements the present invention, including the user computer 102, servers 112, 122, and 142 and the databases 114, 124, and 144. The computer 202 typically comprises a general purpose hardware processor 204A and/or a special purpose hardware processor 204B (hereinafter alternatively collectively referred to as processor 204) and a memory 206, such as random access memory (RAM). The computer 202 may be coupled to other devices, including input/output (I/O) devices such as a keyboard 214, a mouse device 216 and a printer 228.

In one embodiment, the computer 202 operates by the general purpose processor 204A performing instructions defined by the computer program 210 under control of an operating system 208. The computer program 210 and/or the operating system 208 may be stored in the memory 206 and may interface with the user 132 and/or other devices to accept input and commands and, based on such input and commands and the instructions defined by the computer program 210 and operating system 208 to provide output and results. Output/results may be presented on the display 222 or provided to another device for presentation or further processing or action. In one embodiment, the display 222 comprises a liquid crystal display (LCD) having a plurality of separately addressable liquid crystals. Each liquid crystal of the display 222 changes to an opaque or translucent state to form a part of the image on the display in response to the data or information generated by the processor 204 from the application of the instructions of the computer program 210 and/or operating system 208 to the input and commands. The image may be provided through a graphical user interface (GUI) module 218A. Although the GUI module 218A is depicted as a separate module, the instructions performing the GUI functions can be resident or distributed in the operating system 208, the computer program 210, or implemented with special purpose memory and processors.

Some or all of the operations performed by the computer 202 according to the computer program 110 instructions may be implemented in a special purpose processor 204B. In this embodiment, the some or all of the computer program 210 instructions may be implemented via firmware instructions stored in a read only memory (ROM), a programmable read only memory (PROM) or flash memory in within the special purpose processor 204B or in memory 206. The special purpose processor 204B may also be hardwired through circuit design to perform some or all of the operations to implement the present invention. Further, the special purpose processor 204B may be a hybrid processor, which includes dedicated circuitry for performing a subset of functions, and other circuits for performing more general functions such as responding to computer program instructions. In one embodiment, the special purpose processor is an application specific integrated circuit (ASIC).

The computer 202 may also implement a compiler 212 which allows an application program 210 written in a programming language such as COBOL, C++, FORTRAN, or other language to be translated into processor 204 readable code. After completion, the application or computer program 210 accesses and manipulates data accepted from I/O devices and stored in the memory 206 of the computer 202 using the relationships and logic that was generated using the compiler 212. The computer 202 also optionally comprises an external communication device such as a modem, satellite link, Ethernet card, or other device for accepting input from and providing output to other computers.

In one embodiment, instructions implementing the operating system 208, the computer program 210, and the compiler 212 are tangibly embodied in a computer-readable medium, e.g., data storage device 220, which could include one or more fixed or removable data storage devices, such as a zip drive, floppy disc drive 224, hard drive, CD-ROM drive, tape drive, etc. Further, the operating system 208 and the computer program 210 are comprised of computer program instructions which, when accessed, read and executed by the computer 202, causes the computer 202 to perform the steps necessary to implement and/or use the present invention or to load the program of instructions into a memory, thus creating a special purpose data structure causing the computer to operate as a specially programmed computer executing the method steps described herein. Computer program 210 and/or operating instructions may also be tangibly embodied in memory 206 and/or data communications devices 230, thereby making a computer program product or article of manufacture according to the invention. As such, the terms "article of manufacture," "program storage device" and "computer program product" as used herein are intended to encompass a computer program accessible from any computer readable device or media.

Of course, those skilled in the art will recognize that any combination of the above components, or any number of different components, peripherals, and other devices, may be used with the computer 202. Although the term "user computer" is referred to herein, it is understood that a user computer 102 may include portable devices such as medication infusion pumps, analyte sensing apparatuses, cellphones, notebook computers, pocket computers, or any other device with suitable processing, communication, and input/output capability.

Typical Sensor Layers Found in Embodiments of the Invention

Figure 2A:
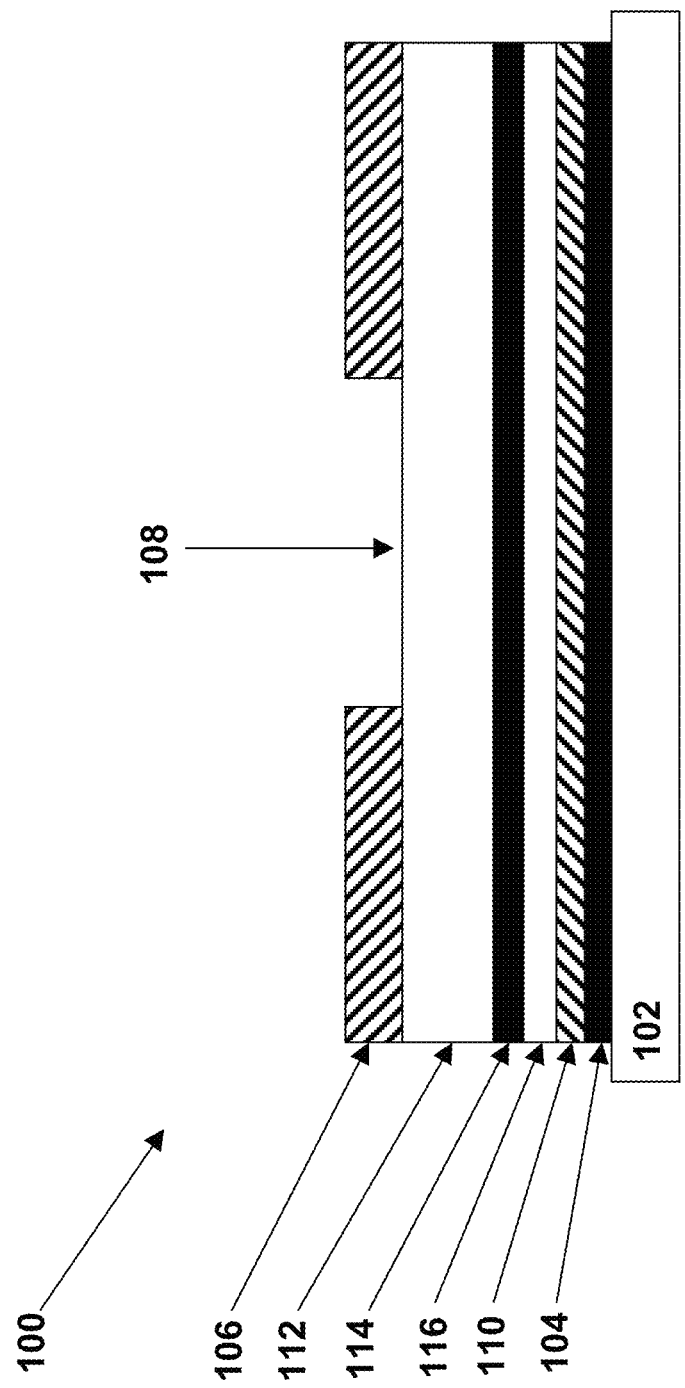
FIG. 2A provides a diagrammatic view of one embodiment of an amperometric analyte sensor to which an interference rejection membrane can be added.
Figure 2B:
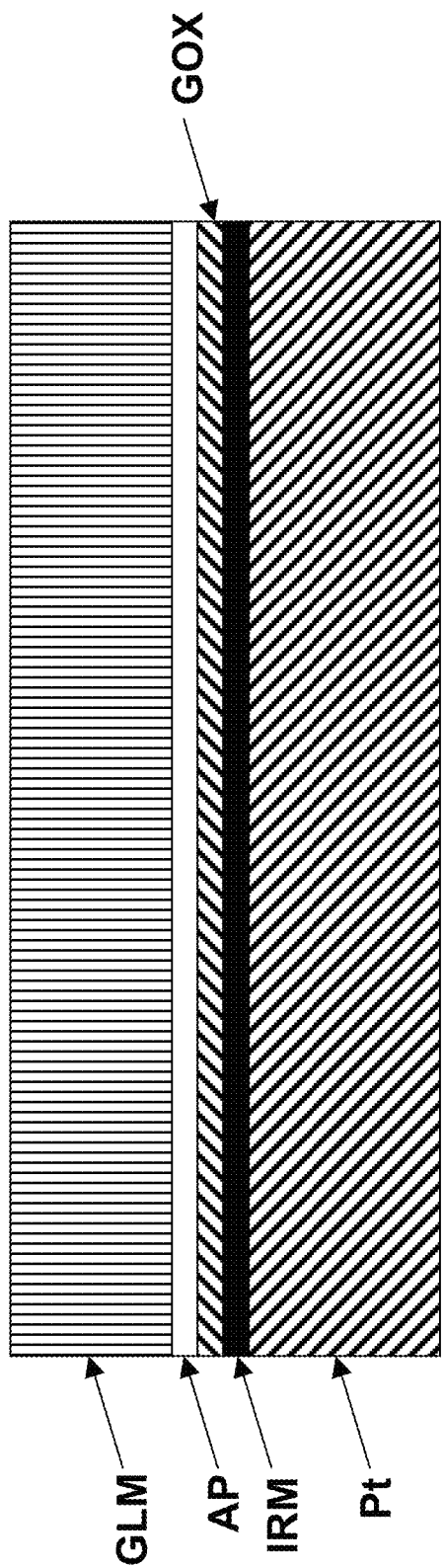
FIG. 2B provides a diagrammatic view of one embodiment of an amperometric analyte sensor having an interference rejection membrane.

As noted above, one or more of the electrodes in the electrode arrays of the invention (e.g. the working electrode) is coated with layers of various compositions that modulate the material properties of these electrode arrays. FIG. 2A illustrates a cross-section of one embodiment 100 of an element of the present invention, one that shows a plurality of layers coating a sensor electrode (e.g. the working electrode). This sensor embodiment is formed from a plurality of components that are typically in the form of layers of various conductive and non-conductive constituents disposed on each other according to art accepted methods and/or the specific methods of the invention disclosed herein. The components of the sensor are typically characterized herein as layers because, for example, it allows for a facile characterization of the sensor structure shown in FIG. 2A. Artisans will understand however, that in certain embodiments of the invention, the sensor constituents are combined such that multiple constituents form one or more heterogeneous layers. In this context, those of skill in the art understand that the ordering of the layered constituents can be altered in various embodiments of the invention.

The embodiment shown in FIG. 2A includes a base layer 102 to support the sensor 100. The base layer 102 can be made of a material such as a metal and/or a ceramic and/or a polymeric substrate, which may be self-supporting or further supported by another material as is known in the art. Embodiments of the invention include a conductive layer 104 which is disposed on and/or combined with the base layer 102. Typically the conductive layer 104 comprises one or more electrodes. An operating sensor 100 typically includes a plurality of electrodes such as a working electrode, a counter electrode and a reference electrode. Other embodiments may also include a plurality of working and/or counter and/or reference electrodes and/or one or more electrodes that performs multiple functions, for example one that functions as both as a reference and a counter electrode.

As discussed in detail below, the base layer 102 and/or conductive layer 104 can be generated using many known techniques and materials. In certain embodiments of the invention, the electrical circuit of the sensor is defined by etching the disposed conductive layer 104 into a desired pattern of conductive paths. A typical electrical circuit for the sensor 100 comprises two or more adjacent conductive paths with regions at a proximal end to form contact pads and regions at a distal end to form sensor electrodes. An electrically insulating cover layer 106 such as a polymer coating can be disposed on portions of the sensor 100. Acceptable polymer coatings for use as the insulating protective cover layer 106 can include, but are not limited to, non-toxic biocompatible polymers such as silicone compounds, polyimides, biocompatible solder masks, epoxy acrylate copolymers, or the like. In the sensors of the present invention, one or more exposed regions or apertures 108 can be made through the cover layer 106 to open the conductive layer 104 to the external environment and to, for example, allow an analyte such as glucose to permeate the layers of the sensor and be sensed by the sensing elements. Apertures 108 can be formed by a number of techniques, including laser ablation, tape masking, chemical milling or etching or photolithographic development or the like. In certain embodiments of the invention, during manufacture, a secondary photoresist can also be applied to the protective layer 106 to define the regions of the protective layer to be removed to form the aperture(s) 108. The exposed electrodes and/or contact pads can also undergo secondary processing (e.g. through the apertures 108), such as additional plating processing, to prepare the surfaces and/or strengthen the conductive regions.

In the sensor configuration shown in FIG. 2A, an analyte sensing layer 110 (which is typically a sensor chemistry layer, meaning that materials in this layer undergo a chemical reaction to produce a signal that can be sensed by the conductive layer) is disposed on one or more of the exposed electrodes of the conductive layer 104. In the sensor configuration shown in FIG. 2B, an interference rejection membrane 120 is disposed on one or more of the exposed electrodes of the conductive layer 104, with the analyte sensing layer 110 then being disposed on this interference rejection membrane 120. Typically, the analyte sensing layer 110 is an enzyme layer. Most typically, the analyte sensing layer 110 comprises an enzyme capable of producing and/or utilizing oxygen and/or hydrogen peroxide, for example the enzyme glucose oxidase. Optionally the enzyme in the analyte sensing layer is combined with a second carrier protein such as human serum albumin, bovine serum albumin or the like. In an illustrative embodiment, an oxidoreductase enzyme such as glucose oxidase in the analyte sensing layer 110 reacts with glucose to produce hydrogen peroxide, a compound which then modulates a current at an electrode. As this modulation of current depends on the concentration of hydrogen peroxide, and the concentration of hydrogen peroxide correlates to the concentration of glucose, the concentration of glucose can be determined by monitoring this modulation in the current. In a specific embodiment of the invention, the hydrogen peroxide is oxidized at a working electrode which is an anode (also termed herein the anodic working electrode), with the resulting current being proportional to the hydrogen peroxide concentration. Such modulations in the current caused by changing hydrogen peroxide concentrations can by monitored by any one of a variety of sensor detector apparatuses such as a universal sensor amperometric biosensor detector or one of the other variety of similar devices known in the art such as glucose monitoring devices produced by Medtronic MiniMed.

In embodiments of the invention, the analyte sensing layer 110 can be applied over portions of the conductive layer or over the entire region of the conductive layer. Typically the analyte sensing layer 110 is disposed on the working electrode which can be the anode or the cathode. Optionally, the analyte sensing layer 110 is also disposed on a counter and/or reference electrode. While the analyte sensing layer 110 can be up to about 1000 microns (µm) in thickness, typically the analyte sensing layer is relatively thin as compared to those found in sensors previously described in the art, and is for example, typically less than 1, 0.5, 0.25 or 0.1 microns in thickness. As discussed in detail below, some methods for generating a thin analyte sensing layer 110 include brushing the layer onto a substrate (e.g. the reactive surface of a platinum black electrode), as well as spin coating processes, dip and dry processes, low shear spraying processes, ink-jet printing processes, silk screen processes and the like.

Typically, the analyte sensing layer 110 is coated and or disposed next to one or more additional layers. Optionally, the one or more additional layers include a protein layer 116 disposed upon the analyte sensing layer 110. Typically, the protein layer 116 comprises a protein such as human serum albumin, bovine serum albumin or the like. Typically, the protein layer 116 comprises human serum albumin. In some embodiments of the invention, an additional layer includes an analyte modulating layer 112 that is disposed above the analyte sensing layer 110 to regulate analyte access with the analyte sensing layer 110. For example, the analyte modulating membrane layer 112 can comprise a glucose limiting membrane, which regulates the amount of glucose that contacts an enzyme such as glucose oxidase that is present in the analyte sensing layer. Such glucose limiting membranes can be made from a wide variety of materials known to be suitable for such purposes, e.g., silicone compounds such as polydimethyl siloxanes, polyurethanes, polyurea cellulose acetates, NAFION, polyester sulfonic acids (e.g. Kodak AQ), hydrogels or any other suitable hydrophilic membranes known to those skilled in the art. In certain embodiments of the invention, the glucose limiting membrane comprises a blended mixture of a linear polyurethane/polyurea polymer, and a branched acrylate polymer as disclosed for example in U.S. patent application Ser. No. 12/643,790, the contents of which are incorporated by reference.

In typical embodiments of the invention, an adhesion promoter layer 114 is disposed between the analyte modulating layer 112 and the analyte sensing layer 110 as shown in FIG. 2 in order to facilitate their contact and/or adhesion. In a specific embodiment of the invention, an adhesion promoter layer 114 is disposed between the analyte modulating layer 112 and the protein layer 116 as shown in FIG. 2 in order to facilitate their contact and/or adhesion. The adhesion promoter layer 114 can be made from any one of a wide variety of materials known in the art to facilitate the bonding between such layers. Typically, the adhesion promoter layer 114 comprises a silane compound. In alternative embodiments, protein or like molecules in the analyte sensing layer 110 can be sufficiently crosslinked or otherwise prepared to allow the analyte modulating membrane layer 112 to be disposed in direct contact with the analyte sensing layer 110 in the absence of an adhesion promoter layer 114.

Embodiments of typical elements used to make the sensors disclosed herein are discussed below.

Typical Analyte Sensor Constituents Used in Embodiments of the Invention

The following disclosure provides examples of typical elements/constituents used in sensor embodiments of the invention. While these elements can be described as discreet units (e.g. layers), those of skill in the art understand that sensors can be designed to contain elements having a combination of some or all of the material properties and/or functions of the elements/constituents discussed below (e.g. an element that serves both as a supporting base constituent and/or a conductive constituent and/or a matrix for the analyte sensing constituent and which further functions as an electrode in the sensor). Those in the art understand that these thin film analyte sensors can be adapted for use in a number of sensor systems such as those described below.

Base Constituent

Sensors of the invention typically include a base constituent (see, e.g. element 102 in FIG. 2A). The term "base constituent" is used herein according to art accepted terminology and refers to the constituent in the apparatus that typically provides a supporting matrix for the plurality of constituents that are stacked on top of one another and comprise the functioning sensor. In one form, the base constituent comprises a thin film sheet of insulative (e.g. electrically insulative and/or water impermeable) material. This base constituent can be made of a wide variety of materials having desirable qualities such as dielectric properties, water impermeability and hermeticity. Some materials include metallic, and/or ceramic and/or polymeric substrates or the like.

The base constituent may be self-supporting or further supported by another material as is known in the art. In one embodiment of the sensor configuration shown in FIG. 2A, the base constituent 102 comprises a ceramic. Alternatively, the base constituent comprises a polymeric material such as a polyimmide. In an illustrative embodiment, the ceramic base comprises a composition that is predominantly $Al_2O_3$ (e.g. 96%). The use of alumina as an insulating base constituent for use with implantable devices is disclosed in U.S. Pat. Nos. 4,940,858, 4,678,868 and 6,472,122 which are incorporated herein by reference. The base constituents of the invention can further include other elements known in the art, for example hermetical vias (see, e.g. WO 03/023388). Depending upon the specific sensor design, the base constituent can be relatively thick constituent (e.g. thicker than 50, 100, 200, 300, 400, 500 or 1000 microns). Alternatively, one can utilize a nonconductive ceramic, such as alumina, in thin constituents, e.g., less than about 30 microns.

Conductive Constituent

The electrochemical sensors of the invention typically include a conductive constituent disposed upon the base constituent that includes at least one electrode for measuring an analyte or its byproduct (e.g. oxygen and/or hydrogen peroxide) to be assayed (see, e.g. element 104 in FIG. 2A). The term "conductive constituent" is used herein according to art accepted terminology and refers to electrically conductive sensor elements such as electrodes which are capable of measuring and a detectable signal and conducting this to a detection apparatus. An illustrative example of this is a conductive constituent that can measure an increase or decrease in current in response to exposure to a stimuli such as the change in the concentration of an analyte or its byproduct as compared to a reference electrode that does not experience the change in the concentration of the analyte, a coreactant (e.g. oxygen) used when the analyte interacts with a composition (e.g. the enzyme glucose oxidase) present in analyte sensing constituent 110 or a reaction product of this interaction (e.g. hydrogen peroxide). Illustrative examples of such elements include electrodes which are capable of producing variable detectable signals in the presence of variable concentrations of molecules such as hydrogen peroxide or oxygen. Typically one of these electrodes in the conductive constituent is a working electrode, which can be made from non-corroding metal or carbon. A carbon working electrode may be vitreous or graphitic and can be made from a solid or a paste. A metallic working electrode may be made from platinum group metals, including palladium or gold, or a non-corroding metallically conducting oxide, such as ruthenium dioxide. Alternatively the electrode may comprise a silver/silver chloride electrode composition. The working electrode may be a wire or a thin conducting film applied to a substrate, for example, by coating or printing. Typically, only a portion of the surface of the metallic or carbon conductor is in electrolytic contact with the analyte-containing solution. This portion is called the working surface of the electrode. The remaining surface of the electrode is typically isolated from the solution by an electrically insulating cover constituent 106. Examples of useful materials for generating this protective cover constituent 106 include polymers such as polyimides, polytetrafluoroethylene, polyhexafluoropropylene and silicones such as polysiloxanes.

In addition to the working electrode, the analyte sensors of the invention typically include a reference electrode or a combined reference and counter electrode (also termed a quasi-reference electrode or a counter/reference electrode). If the sensor does not have a counter/reference electrode then it may include a separate counter electrode, which may be made from the same or different materials as the working electrode. Typical sensors of the present invention have one or more working electrodes and one or more counter, reference, and/or counter/reference electrodes. One embodiment of the sensor of the present invention has two, three or four or more working electrodes. These working electrodes in the sensor may be integrally connected or they may be kept separate.

Typically for in vivo use, embodiments of the present invention are implanted subcutaneously in the skin of a mammal for direct contact with the body fluids of the mammal, such as blood. Alternatively the sensors can be implanted into other regions within the body of a mammal such as in the intraperotineal space. When multiple working electrodes are used, they may be implanted together or at different positions in the body. The counter, reference, and/or counter/reference electrodes may also be implanted either proximate to the working electrode(s) or at other positions within the body of the mammal. Embodiments of the invention include sensors comprising electrodes constructed from nanostructured materials. As used herein, a "nanostructured material" is an object manufactured to have at least one dimension smaller than 100 nm. Examples include, but are not limited to, single-walled nanotubes, double-walled nanotubes, multi-walled nanotubes, bundles of nanotubes, fullerenes, cocoons, nanowires, nanofibres, onions and the like.

Interference Rejection Constituent

The electrochemical sensors of the invention optionally include an interference rejection constituent disposed between the surface of the electrode and the environment to be assayed. In particular, certain sensor embodiments rely on the oxidation and/or reduction of hydrogen peroxide generated by enzymatic reactions on the surface of a working electrode at a constant potential applied. Because amperometric detection based on direct oxidation of hydrogen peroxide requires a relatively high oxidation potential, sensors employing this detection scheme may suffer interference from oxidizable species that are present in biological fluids such as ascorbic acid, uric acid and acetaminophen. In this context, the term "interference rejection constituent" is used herein according to art accepted terminology and refers to a coating or membrane in the sensor that functions to inhibit spurious signals generated by such oxidizable species which interfere with the detection of the signal generated by the analyte to be sensed. Certain interference rejection constituents function via size exclusion (e.g. by excluding interfering species of a specific size). Examples of interference rejection constituents include one or more layers or coatings of compounds such as the hydrophilic crosslinked pHEMA and polylysine polymers disclosed in U.S. patent application Ser. No. 12/572,087, the contents of which are incorporated by reference, as well as cellulose acetate (including cellulose acetate incorporating agents such as poly(ethylene glycol)), polyethersulfones, polytetra-fluoroethylenes, the perfluoronated ionomer NAFION, polyphenylenediamine, epoxy and the like.

Analyte Sensing Constituent

The electrochemical sensors of the invention include an analyte sensing constituent disposed on the electrodes of the sensor (see, e.g. element 110 in FIG. 2A). The term "analyte sensing constituent" is used herein according to art accepted terminology and refers to a constituent comprising a material that is capable of recognizing or reacting with an analyte whose presence is to be detected by the analyte sensor apparatus. Typically this material in the analyte sensing constituent produces a detectable signal after interacting with the analyte to be sensed, typically via the electrodes of the conductive constituent. In this regard the analyte sensing constituent and the electrodes of the conductive constituent work in combination to produce the electrical signal that is read by an apparatus associated with the analyte sensor. Typically, the analyte sensing constituent comprises an oxidoreductase enzyme capable of reacting with and/or producing a molecule whose change in concentration can be measured by measuring the change in the current at an electrode of the conductive constituent (e.g. oxygen and/or hydrogen peroxide), for example the enzyme glucose oxidase. An enzyme capable of producing a molecule such as hydrogen peroxide can be disposed on the electrodes according to a number of processes known in the art. The analyte sensing constituent can coat all or a portion of the various electrodes of the sensor. In this context, the analyte sensing constituent may coat the electrodes to an equivalent degree. Alternatively the analyte sensing constituent may coat different electrodes to different degrees, with for example the coated surface of the working electrode being larger than the coated surface of the counter and/or reference electrode.

Typical sensor embodiments of this element of the invention utilize an enzyme (e.g. glucose oxidase) that has been combined with a second protein (e.g. albumin) in a fixed ratio (e.g. one that is typically optimized for glucose oxidase stabilizing properties) and then applied on the surface of an electrode to form a thin enzyme constituent. In a typical embodiment, the analyte sensing constituent comprises a GOx and HSA mixture. In a typical embodiment of an analyte sensing constituent having GOx, the GOx reacts with glucose present in the sensing environment (e.g. the body of a mammal) and generates hydrogen peroxide according to the reaction shown in FIG. 1, wherein the hydrogen peroxide so generated is anodically detected at the working electrode in the conductive constituent.

As noted above, the enzyme and the second protein (e.g. an albumin) are typically treated to form a crosslinked matrix (e.g. by adding a cross-linking agent to the protein mixture). As is known in the art, crosslinking conditions may be manipulated to modulate factors such as the retained biological activity of the enzyme, its mechanical and/or operational stability. Illustrative crosslinking procedures are described in U.S. patent application Ser. No. 10/335,506 and PCT publication WO 03/035891 which are incorporated herein by reference. For example, an amine cross-linking reagent, such as, but not limited to, glutaraldehyde, can be added to the protein mixture.

Protein Constituent

The electrochemical sensors of the invention optionally include a protein constituent disposed between the analyte sensing constituent and the analyte modulating constituent (see, e.g. element 116 in FIG. 2A). The term "protein constituent" is used herein according to art accepted terminology and refers to constituent containing a carrier protein or the like that is selected for compatibility with the analyte sensing constituent and/or the analyte modulating constituent. In typical embodiments, the protein constituent comprises an albumin such as human serum albumin. The HSA concentration may vary between about 0.5%-30% (w/v). Typically the HSA concentration is about 1-10% w/v, and most typically is about 5% w/v. In alternative embodiments of the invention, collagen or BSA or other structural proteins used in these contexts can be used instead of or in addition to HSA. This constituent is typically crosslinked on the analyte sensing constituent according to art accepted protocols.

Adhesion Promoting Constituent

The electrochemical sensors of the invention can include one or more adhesion promoting (AP) constituents (see, e.g. element 114 in FIG. 2A). The term "adhesion promoting constituent" is used herein according to art accepted terminology and refers to a constituent that includes materials selected for their ability to promote adhesion between adjoining constituents in the sensor. Typically, the adhesion promoting constituent is disposed between the analyte sensing constituent and the analyte modulating constituent. Typically, the adhesion promoting constituent is disposed between the optional protein constituent and the analyte modulating constituent. The adhesion promoter constituent can be made from any one of a wide variety of materials known in the art to facilitate the bonding between such constituents and can be applied by any one of a wide variety of methods known in the art. Typically, the adhesion promoter constituent comprises a silane compound such as γ-aminopropyltrimethoxysilane.

The use of silane coupling reagents, especially those of the formula $R'Si(OR)_3$ in which R' is typically an aliphatic group with a terminal amine and R is a lower alkyl group, to promote adhesion is known in the art (see, e.g. U.S. Pat. No. 5,212,050 which is incorporated herein by reference). For example, chemically modified electrodes in which a silane such as γ-aminopropyltriethoxysilane and glutaraldehyde were used in a step-wise process to attach and to co-crosslink bovine serum albumin (BSA) and glucose oxidase ($GO_x$) to the electrode surface are well known in the art (see, e.g. Yao, T. Analytica Chim. Acta 1983, 148, 27-33).

In certain embodiments of the invention, the adhesion promoting constituent further comprises one or more compounds that can also be present in an adjacent constituent such as the polydimethyl siloxane (PDMS) compounds that serves to limit the diffusion of analytes such as glucose through the analyte modulating constituent. In illustrative embodiments the formulation comprises 0.5-20% PDMS, typically 5-15% PDMS, and most typically 10% PDMS. In certain embodiments of the invention, the adhesion promoting constituent is crosslinked within the layered sensor system and correspondingly includes an agent selected for its ability to crosslink a moiety present in a proximal constituent such as the analyte modulating constituent. In illustrative embodiments of the invention, the adhesion promoting constituent includes an agent selected for its ability to crosslink an amine or carboxyl moiety of a protein present in a proximal constituent such a the analyte sensing constituent and/or the protein constituent and or a siloxane moiety present in a compound disposed in a proximal layer such as the analyte modulating layer.

Analyte Modulating Constituent

The electrochemical sensors of the invention include an analyte modulating constituent disposed on the sensor (see, e.g. element 112 in FIG. 2A). The term "analyte modulating constituent" is used herein according to art accepted terminology and refers to a constituent that typically forms a membrane on the sensor that operates to modulate the diffusion of one or more analytes, such as glucose, through the constituent. In certain embodiments of the invention, the analyte modulating constituent is an analyte-limiting membrane (e.g. a glucose limiting membrane) which operates to prevent or restrict the diffusion of one or more analytes, such as glucose, through the constituents. In other embodiments of the invention, the analyte-modulating constituent operates to facilitate the diffusion of one or more analytes, through the constituents. Optionally such analyte modulating constituents can be formed to prevent or restrict the diffusion of one type of molecule through the constituent (e.g. glucose), while at the same time allowing or even facilitating the diffusion of other types of molecules through the constituent (e.g. $O_2$).

With respect to glucose sensors, in known enzyme electrodes, glucose and oxygen from blood, as well as some interferents, such as ascorbic acid and uric acid, diffuse through a primary membrane of the sensor. As the glucose, oxygen and interferents reach the analyte sensing constituent, an enzyme, such as glucose oxidase, catalyzes the conversion of glucose to hydrogen peroxide and gluconolactone. The hydrogen peroxide may diffuse back through the analyte modulating constituent, or it may diffuse to an electrode where it can be reacted to form oxygen and a proton to produce a current that is proportional to the glucose concentration. The sensor membrane assembly serves several functions, including selectively allowing the passage of glucose therethrough. In this context, an illustrative analyte modulating constituent is a semi-permeable membrane which permits passage of water, oxygen and at least one selective analyte and which has the ability to absorb water, the membrane having a water soluble, hydrophilic polymer.

A variety of illustrative analyte modulating compositions are known in the art and are described for example in U.S. patent application Ser. No. 12/643,790, U.S. Pat. Nos. 6,319, 540, 5,882,494, 5,786,439 5,777,060, 5,771,868 and 5,391, 250, and U.S. patent application Ser. No. 12/643,790, the disclosures of each being incorporated herein by reference. In certain embodiments of the invention, the analyte modulating layer comprises a blended mixture of a linear polyurethane/polyurea polymer, and a branched acrylate polymer that are blended together at a ratio of between 1:1 and 1:20 by weight %. In one illustrative embodiment, the analyte modulating layer comprises a polyurethane/polyurea polymer formed from a mixture comprising a diisocyanate; a hydrophilic polymer comprising a hydrophilic diol or hydrophilic diamine; and a siloxane having an amino, hydroxyl or carboxylic acid functional group at a terminus that is blended together in a 1:1 to 1:2 ratio with a branched acrylate polymer formed from a mixture comprising a butyl, propyl, ethyl or methyl-acrylate; an amino-acrylate; and a siloxane-acrylate; and a poly(ethylene oxide)-acrylate.

Cover Constituent

The electrochemical sensors of the invention include one or more cover constituents which are typically electrically insulating protective constituents (see, e.g. element 106 in FIG. 2A). Typically, such cover constituents can be in the form of a coating, sheath or tube and are disposed on at least a portion of the analyte modulating constituent. Acceptable polymer coatings for use as the insulating protective cover constituent can include, but are not limited to, non-toxic biocompatible polymers such as silicone compounds, polyimides, biocompatible solder masks, epoxy acrylate copolymers, or the like. Further, these coatings can be photo-imageable to facilitate photolithographic forming of apertures through to the conductive constituent. A typical cover constituent comprises spun on silicone. As is known in the art, this constituent can be a commercially available RTV (room temperature vulcanized) silicone composition. A typical chemistry in this context is polydimethyl siloxane (acetoxy based).

Typical Analyte Sensor System Embodiments of the Invention

Embodiments of the sensor elements and sensors disclosed herein can be operatively coupled to a variety of other systems elements typically used with analyte sensors (e.g. structural elements such as piercing members, insertion sets and the like as well as electronic components such as processors, monitors, medication infusion pumps and the like), for example to adapt them for use in various contexts (e.g. implantation within a mammal). One embodiment of the invention includes a method of monitoring a physiological characteristic of a user using an embodiment of the invention that includes four input elements capable of receiving signals from four sensor arrays (i.e. signals based on a sensed physiological characteristic value of the user), and a processor for analyzing the four received signals. In typical embodiments of the invention, the processor determines a dynamic behavior of the physiological characteristic value and provides an observable indicator based upon the dynamic behavior of the physiological characteristic value so determined. In some embodiments, the physiological characteristic value is a measure of the concentration of blood glucose in the user. In other embodiments, the process of analyzing the received signal and determining a dynamic behavior includes repeatedly measuring the physiological characteristic value to obtain a series of physiological characteristic values in order to, for example, incorporate comparative redundancies into a sensor apparatus in a manner designed to provide confirmatory information on sensor function, analyte concentration measurements, the presence of interferences and the like.

Embodiments of the invention include devices which display data from measurements of a sensed physiological characteristic (e.g. blood glucose concentrations) in a manner and format tailored to allow a user of the device to easily monitor and, if necessary, modulate the physiological status of that characteristic (e.g. modulation of blood glucose concentrations via insulin administration). An illustrative embodiment of the invention is a device comprising a sensor input capable of receiving a signal from a sensor, the signal being based on a sensed physiological characteristic value of a user; a memory for storing a plurality of measurements of the sensed physiological characteristic value of the user from the received signal from the sensor; and a display for presenting a text and/or graphical representation of the plurality of measurements of the sensed physiological characteristic value (e.g. text, a line graph or the like, a bar graph or the like, a grid pattern or the like or a combination thereof). Typically, the graphical representation displays real time measurements of the sensed physiological characteristic value. Such devices can be used in a variety of contexts, for example in combination with other medical apparatuses. In some embodiments of the invention, the device is used in combination with at least one other medical device (e.g. a glucose sensor).

An illustrative system embodiment consists of a glucose sensor, a transmitter and pump receiver and a glucose meter. In this system, radio signals from the transmitter can be sent to the pump receiver periodically (e.g. every 5 minutes) to provide providing real-time sensor glucose (SG) values. Values/graphs are displayed on a monitor of the pump receiver so that a user can self monitor blood glucose and deliver insulin using their own insulin pump. Typically an embodiment of device disclosed herein communicates with a second medical device via a wired or wireless connection. Wireless communication can include for example the reception of emitted radiation signals as occurs with the transmission of signals via RF telemetry, infrared transmissions, optical transmission, sonic and ultrasonic transmissions and the like. Optionally, the device is an integral part of a medication infusion pump (e.g. an insulin pump). Typically in such devices, the physiological characteristic values includes a plurality of measurements of blood glucose.

Embodiments of the Invention and Associated Characteristics

Embodiments of the invention disclosed herein focus on sensor systems having four independent sensor arrays, algorithms used with such arrays and/or materials and configurations of elements that facilitate the characterization of analyte concentrations in vivo. Embodiments of the invention can be used for example to examine sensor interference and sensor drift as well as sensor initialization and/or start-up in vivo (e.g. the run-in time that it takes for a sensor to settle into its aqueous environment and start transmitting meaningful information after being implanted in vivo). In particular, it is known in the art that the amount of time required for sensor initialization and/or start-up prior to its use can be relatively long (e.g. in amperometric glucose sensors, the sensor start-up initialization times can range from 2 to 10 hours), a factor which can hinder the use of such sensors in the administration of medical care. For example, in hospital settings, a relatively long sensor initialization and/or start-up period can delay the receipt of important information relating to patient health (e.g. hyperglycemia or hypoglycemia in a diabetic patient), thereby delaying treatments predicated on the receipt of such information (e.g. the administration of insulin). In addition, a relatively long sensor initialization and/or start-up period in hospital settings can require repeated monitoring by hospital staff, a factor which contributes to the costs of patient care. For these reasons, sensors having reduced initialization and/or start-up times in vivo in hospital settings and sensors and sensor systems that are designed to include elements and/or configurations of elements that diminish long sensor initialization and/or start-up times are highly desirable. With glucose sensors for example, a 15-30 minute reduction of sensor initialization and/or start-up time is highly desirable because, for example, such shorter initialization times can: (1) reduce the need for patient monitoring by hospital personnel, a factor which contributes to the cost-effectiveness of such medical devices; and (2) reduce delays in the receipt of important information relating to patient health.

In individuals using analyte sensors in non-hospital settings (e.g. diabetics using glucose sensors to manage their disease), relatively long sensor initialization and/or start-up periods are also problematical due to both the inconvenience to the user as well as the delayed receipt of information relating to user health. The use of glucose sensors, insulin infusion pumps and the like in the management of diabetes has increased in recent years due for example to studies showing that the morbidity and mortality issues associated with this chronic disease decrease dramatically when a patient administers insulin in a manner that closely matches the rise and fall of physiological insulin concentrations in healthy individuals. Consequently, patients who suffer from chronic diseases such as diabetes are instructed by medical personnel to play an active role in the management of their disease, in particular, the close monitoring and modulation of blood glucose levels. In this context, because many diabetics do not have medical training, they may forgo optimal monitoring and modulation of blood glucose levels due to complexities associated with such management, for example, a two hour start-up period which can be an inconvenience in view of a patient's active daily routine. For these reasons, sensors and sensor systems that are designed to include elements and/or configurations of elements can reduce sensor initialization and/or start-up times are highly desirable in situations where such sensors are operated by a diabetic patient without medical training because they facilitate the patient's convenient management of their disease, behavior which is shown to decrease the well known morbidity and mortality issues observed in individuals suffering from chronic diabetes.

While the analyte sensor and sensor systems disclosed herein are typically designed to be implantable within the body of a mammal, the inventions disclosed herein are not limited to any particular environment and can instead be used in a wide variety of contexts, for example for the analysis of most in vivo and in vitro liquid samples including biological fluids such as interstitial fluids, whole-blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate or the like. In addition, solid or desiccated samples may be dissolved in an appropriate solvent to provide a liquid mixture suitable for analysis.

Illustrative Methods and Materials for Making Analyte Sensor Apparatus of the Invention A number of articles, U.S. patents and patent application describe the state of the art with the common methods and materials disclosed herein and further describe various elements (and methods for their manufacture) that can be used in the sensor designs disclosed herein. These include for example, U.S. Pat. Nos. 6,413,393; 6,368,274; 5,786,439; 5,777,060; 5,391,250; 5,390,671; 5,165,407, 4,890,620, 5,390,671, 5,390,691, 5,391,250, 5,482,473, 5,299,571, 5,568,806; United States Patent Application 20020090738; as well as PCT International Publication Numbers WO 01/58348, WO 03/034902, WO 03/035117, WO 03/035891, WO 03/023388, WO 03/022128, WO 03/022352, WO 03/023708, WO 03/036255, WO03/036310 and WO 03/074107, the contents of each of which are incorporated herein by reference.

Typical sensors for monitoring glucose concentration of diabetics are further described in Shichiri, et al.: "In Vivo Characteristics of Needle-Type Glucose Sensor-Measurements of Subcutaneous Glucose Concentrations in Human Volunteers," Horm. Metab. Res., Suppl. Ser. 20:17-20 (1988); Bruckel, et al.: "In Vivo Measurement of Subcutaneous Glucose Concentrations with an Enzymatic Glucose Sensor and a Wick Method," Klin. Wochenschr. 67:491-495 (1989); and Pickup, et al.: "In Vivo Molecular Sensing in Diabetes Mellitus: An Implantable Glucose Sensor with Direct Electron Transfer," Diabetologia 32:213-217 (1989). Other sensors are described in, for example Reach, et al., in ADVANCES IN IMPLANTABLE DEVICES, A. Turner (ed.), JAI Press, London, Chap. 1, (1993), incorporated herein by reference.

General Methods for Making Analyte Sensors

A typical embodiment of the invention disclosed herein is a method of making a sensor electrode array for implantation within a mammal, for example one comprising the steps of: providing a base layer; forming a conductive layer on the base layer, wherein the conductive layer includes an electrode (and typically a working electrode, a reference electrode and a counter electrode); forming a interference rejection membrane on the conductive layer, forming an analyte sensing layer on the interference rejection membrane, wherein the analyte sensing layer includes a composition that can alter the electrical current at the electrode in the conductive layer in the presence of an analyte; optionally forming a protein layer on the analyte sensing layer; forming an adhesion promoting layer on the analyte sensing layer or the optional protein layer; forming an analyte modulating layer disposed on the adhesion promoting layer, wherein the analyte modulating layer includes a composition that modulates the diffusion of the analyte therethrough; and forming a cover layer disposed on at least a portion of the analyte modulating layer, wherein the cover layer further includes an aperture over at least a portion of the analyte modulating layer. In embodiments of the invention, four sensor arrays can be disposed on two probes which are releasably coupled to a probes platform. In certain embodiments of the invention, the analyte modulating layer comprises a hydrophilic comb-copolymer having a central chain and a plurality of side chains coupled to the central chain, wherein at least one side chain comprises a silicone moiety. In some embodiments of these methods, the analyte sensor apparatus is formed in a planar geometric configuration As disclosed herein, the various layers of the sensor can be manufactured to exhibit a variety of different characteristics which can be manipulated according to the specific design of the sensor. For example, the adhesion promoting layer includes a compound selected for its ability to stabilize the overall sensor structure, typically a silane composition. In some embodiments of the invention, the analyte sensing layer is formed by a spin coating process and is of a thickness selected from the group consisting of less than 1, 0.5, 0.25 and 0.1 microns in height.

Typically, a method of making the sensor includes the step of forming a protein layer on the analyte sensing layer, wherein a protein within the protein layer is an albumin selected from the group consisting of bovine serum albumin and human serum albumin. Typically, a method of making the sensor includes the step of forming an analyte sensing layer that comprises an enzyme composition selected from the group consisting of glucose oxidase, glucose dehydrogenase, lactate oxidase, hexokinase and lactate dehydrogenase. In such methods, the analyte sensing layer typically comprises a carrier protein composition in a substantially fixed ratio with the enzyme, and the enzyme and the carrier protein are distributed in a substantially uniform manner throughout the analyte sensing layer.

Typical Protocols and Materials Useful in the Manufacture of Analyte Sensors

The disclosure provided herein includes sensors and sensor designs that can be generated using combinations of various well known techniques. The disclosure further provides methods for applying very thin enzyme coatings to these types of sensors as well as sensors produced by such processes. In this context, some embodiments of the invention include methods for making such sensors on a substrate according to art accepted processes. In certain embodiments, the substrate comprises a rigid and flat structure suitable for use in photolithographic mask and etch processes. In this regard, the substrate typically defines an upper surface having a high degree of uniform flatness. A polished glass plate may be used to define the smooth upper surface. Alternative substrate materials include, for example, stainless steel, aluminum, and plastic materials such as delrin, etc. In other embodiments, the substrate is non-rigid and can be another layer of film or insulation that is used as a substrate, for example plastics such as polyimides and the like.

An initial step in the methods of the invention typically includes the formation of a base layer of the sensor. The base layer can be disposed on the substrate by any desired means, for example by controlled spin coating. In addition, an adhesive may be used if there is not sufficient adhesion between the substrate layer and the base layer. A base layer of insulative material is formed on the substrate, typically by applying the base layer material onto the substrate in liquid form and thereafter spinning the substrate to yield the base layer of thin, substantially uniform thickness. These steps are repeated to build up the base layer of sufficient thickness, followed by a sequence of photolithographic and/or chemical mask and etch steps to form the conductors discussed below. In an illustrative form, the base layer comprises a thin film sheet of insulative material, such as ceramic or polyimide substrate. The base layer can comprise an alumina substrate, a polyimide substrate, a glass sheet, controlled pore glass, or a planarized plastic liquid crystal polymer. The base layer may be derived from any material containing one or more of a variety of elements including, but not limited to, carbon, nitrogen, oxygen, silicon, sapphire, diamond, aluminum, copper, gallium, arsenic, lanthanum, neodymium, strontium, titanium, yttrium, or combinations thereof. Additionally, the substrate may be coated onto a solid support by a variety of methods well-known in the art including physical vapor deposition, or spin-coating with materials such as spin glasses, chalcogenides, graphite, silicon dioxide, organic synthetic polymers, and the like.

The methods of the invention further include the generation of a conductive layer having one or more sensing elements. Typically these sensing elements are electrodes that are formed by one of the variety of methods known in the art such as photoresist, etching and rinsing to define the geometry of the active electrodes. The electrodes can then be made electrochemically active, for example by electrodeposition of Pt black for the working and counter electrode, and silver followed by silver chloride on the reference electrode. A sensor layer such as a analyte sensing enzyme layer can then be disposed on the sensing layer by electrochemical deposition or a method other than electrochemical deposition such a spin coating, followed by vapor crosslinking, for example with a dialdehyde (glutaraldehyde) or a carbodi-imide.

Electrodes of the invention can be formed from a wide variety of materials known in the art. For example, the electrode may be made of a noble late transition metals. Metals such as gold, platinum, silver, rhodium, iridium, ruthenium, palladium, or osmium can be suitable in various embodiments of the invention. Other compositions such as carbon or mercury can also be useful in certain sensor embodiments. Of these metals, silver, gold, or platinum is typically used as a reference electrode metal. A silver electrode which is subsequently chloridized is typically used as the reference electrode. These metals can be deposited by any means known in the art, including the plasma deposition method cited, supra, or by an electroless method which may involve the deposition of a metal onto a previously metallized region when the substrate is dipped into a solution containing a metal salt and a reducing agent. The electroless method proceeds as the reducing agent donates electrons to the conductive (metallized) surface with the concomitant reduction of the metal salt at the conductive surface. The result is a layer of adsorbed metal. (For additional discussions on electroless methods, see: Wise, E. M. Palladium: Recovery, Properties, and Uses, Academic Press, New York, N.Y. (1988); Wong, K. et al. Plating and Surface Finishing 1988, 75, 70-76; Matsuoka, M. et al. Ibid. 1988, 75, 102-106; and Pearlstein, F. "Electroless Plating," Modern Electroplating, Lowenheim, F. A., Ed., Wiley, New York, N.Y. (1974), Chapter 31). Such a metal deposition process must yield a structure with good metal to metal adhesion and minimal surface contamination, however, to provide a catalytic metal electrode surface with a high density of active sites. Such a high density of active sites is a property necessary for the efficient redox conversion of an electroactive species such as hydrogen peroxide.

In an exemplary embodiment of the invention, the base layer is initially coated with a thin film conductive layer by electrode deposition, surface sputtering, or other suitable process step. In one embodiment this conductive layer may be provided as a plurality of thin film conductive layers, such as an initial chrome-based layer suitable for chemical adhesion to a polyimide base layer followed by subsequent formation of thin film gold-based and chrome-based layers in sequence. In alternative embodiments, other electrode layer conformations or materials can be used. The conductive layer is then covered, in accordance with conventional photolithographic techniques, with a selected photoresist coating, and a contact mask can be applied over the photoresist coating for suitable photoimaging. The contact mask typically includes one or more conductor trace patterns for appropriate exposure of the photoresist coating, followed by an etch step resulting in a plurality of conductive sensor traces remaining on the base layer. In an illustrative sensor construction designed for use as a subcutaneous glucose sensor, each sensor trace can include three parallel sensor elements corresponding with three separate electrodes such as a working electrode, a counter electrode and a reference electrode.

Portions of the conductive sensor layers are typically covered by an insulative cover layer, typically of a material such as a silicon polymer and/or a polyimide. The insulative cover layer can be applied in any desired manner. In an exemplary procedure, the insulative cover layer is applied in a liquid layer over the sensor traces, after which the substrate is spun to distribute the liquid material as a thin film overlying the sensor traces and extending beyond the marginal edges of the sensor traces in sealed contact with the base layer. This liquid material can then be subjected to one or more suitable radiation and/or chemical and/or heat curing steps as are known in the art. In alternative embodiments, the liquid material can be applied using spray techniques or any other desired means of application. Various insulative layer materials may be used such as photoimagable epoxyacrylate, with an illustrative material comprising a photoimagable polyimide available from OCG, Inc. of West Paterson, N.J., under the product number 7020.

Kits and Sensor Sets of the Invention

In another embodiment of the invention, a kit and/or sensor set, useful for the sensing an analyte as is described above, is provided. The kit and/or sensor set typically comprises a container, a label and an analyte sensor as described above. Suitable containers include, for example, an easy to open package made from a material such as a metal foil, bottles, vials, syringes, and test tubes. The containers may be formed from a variety of materials such as metals (e.g. foils) paper products, glass or plastic. The label on, or associated with, the container indicates that the sensor is used for assaying the analyte of choice. In some embodiments, the container holds device including a probe platform coupled to two probes, each having two electrode arrays comprising a working, counter and reference electrode, wherein these electrode arrays are configured to be electronically independent of one another. The kit and/or sensor set may further include other materials desirable from a commercial and user standpoint, including elements or devices designed to facilitate the introduction of the sensor into the analyte environment, other buffers, diluents, filters, needles, syringes, and package inserts with instructions for use.

Various publication citations are referenced throughout the specification. In addition, certain text from related art is reproduced herein to more clearly delineate the various embodiments of the invention. The disclosures of all citations in the specification are expressly incorporated herein by reference.

EXAMPLES

Example 1

Illustrative Structure for a Hospital Glucose Sensor

In typical hospital sensor embodiments, there are two sensor probes that are inserted in vivo. Each probe contains two sensor arrays with each array comprising a working, counter and reference electrode. Each array is a full glucose sensor electrode system, thus on a single hospital sensor it is comprised of a total of four independent glucose sensor electrode arrays.

Figure 2C:
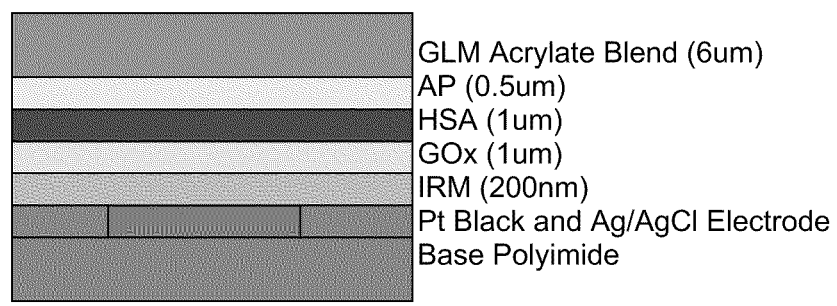
FIG. 2C provides a diagrammatic view of a specific embodiment of an amperometric glucose sensor having a plurality of layers including a layer of a glucose limiting membrane (GLM), a layer of an adhesion promoter, a layer of human serum albumin (HSA), a layer of glucose oxidase, a layer of an interference rejection membrane (IRM), and an electrode layer, all of which are supported by a base comprised of a polyimide composition.

One illustrative layer of functional compositions that is disposed on an electrode within an electrode array is illustrated in FIG. 2C. The IRM is comprised of pHEMA and silane and is deposited using a spray application. A thicker layer of IRM is typically applied on the hospital sensor to reduce the response to 20 mg/dL acetaminophen. This sensor with this IRM has a 50% response to 20 mg/dL acetaminophen.

The analyte modulating layer in this sensor comprises a glucose limiting membrane (GLM). The GLM layer comprises a blended mixture of a linear polyurethane/polyurea polymer, and a branched acrylate polymer. Both polymer compositions are blended together at a ratio of between 1:1 to 1:2 (e.g. 1 part linear polyurethane/polyurea polymer, and 1.5 parts of branched acrylate polymer). Blending the polymers allows for the titration of glucose diffusion to the electrode. By using this blending composition, a higher signal sensor can be produced while preventing glucose saturation from occurring. A high signal sensor benefit from a larger signal to noise ratio thus giving improved sensor accuracy in the hypoglycemic region which is critical for the hospital environment.

For the platinum plating on the sensor, the electrodes are overplated. In the case of the Hospital Sensor, overplating has shown improvement in animal studies where the sensor is much more responsive than those made with electrodes formed from conventional electroplating processes.

Example 2

Illustrative Continuous Glucose Monitoring Algorithm

In certain embodiments of the invention, the continuous glucose monitoring (HCGM) system consists of a quad-sensor (four sensors as a set), a sensor processor and a monitor. All of the four sensors in the quad-sensor set are electrochemical sensors with three electrodes: a working electrode, a reference electrode and a counter electrode. There are two groups of sensors in the quad-sensor set. In one group, the sensors have a first "full-sized" working electrode with a first electroactive area. They are called full-size sensors (FSS). In the other group, the sensors' working electrode is half of the size of the FSS. They are called half-size sensors (HSS). In the quad-sensor set, there are two sensors in FSS group and two sensors in HSS group. Each of the four sensors will generate two signals. One is the current signal Isig, which measures the response of the sensor to the glucose level. The other is the voltage signal Vcounter (or abbreviated as Vcntr), which is the voltage as applied on the counter electrode. Due to the larger working electrode size, FSS is more sensitive in hypoglycemia region. Also, the Isig signal amplitude of FSS is roughly double that of HSS, due to double-sized working electrode. In this embodiment, FSS is the working horse while HSS exists to enhance the redundancy of the quad-sensor set.

In this embodiment, a processor will power the quad-sensor. It will also read the signals from the quad-sensor, convert them from analog to digital format. When the processor is connected to the monitor, it will transmit the signals to the monitor for processing. Otherwise, the processor can store certain amount of data on board for further processing. The monitor in this embodiment contains the major software components of the system: the system control logic, GUI, tight glucose control (TGC) module and ICF (Integrity Check, Calibration scheme, sensor Fusion) module. The system control logic will control the running of the HCGM system. Users use GUI to interact and control the system. TGC will determine the insulin dosing based on the glucose measured. ICF will process the sensor signals.

ICF Functionalities

Figure 6A:
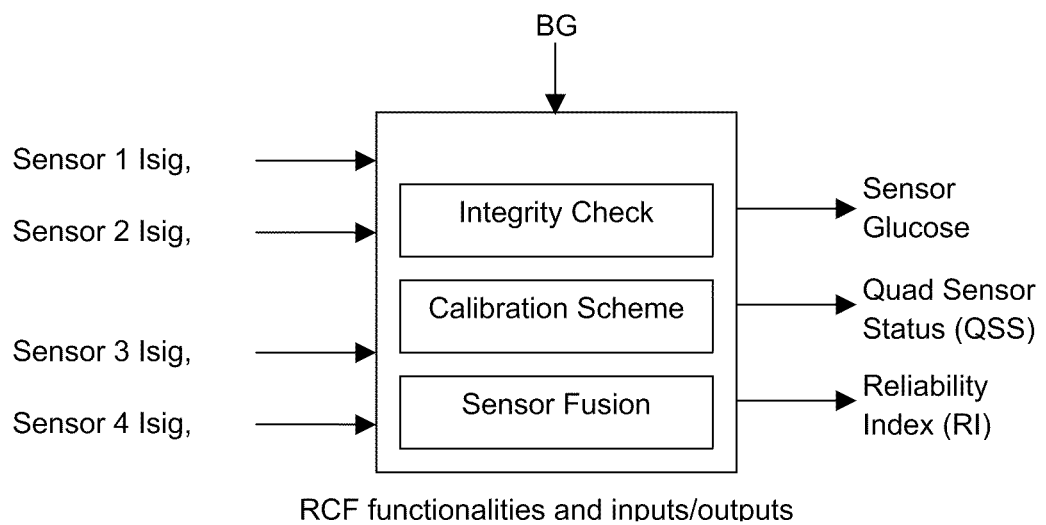
FIG. 6A provides a flowchart showing the basic functionalities and inputs/outputs of an illustrative ICF (Integrity Check, Calibration scheme, sensor Fusion) module. All the signals from the two groups of sensors will be processed by ICF. Thus, four Isig signals and four Vcntr signals, will be fed into the ICF for processing.
Figure 6B:
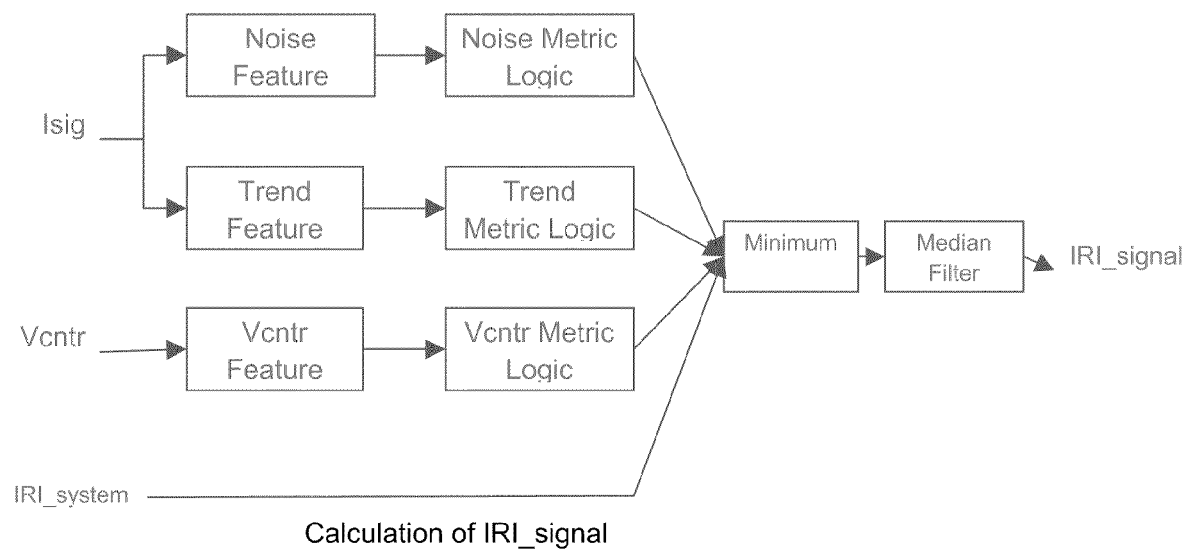
FIG. 6B provides a flowchart showing the calculation procedure of an internal reliability index signal (IRI_signal).
Figure 6C:
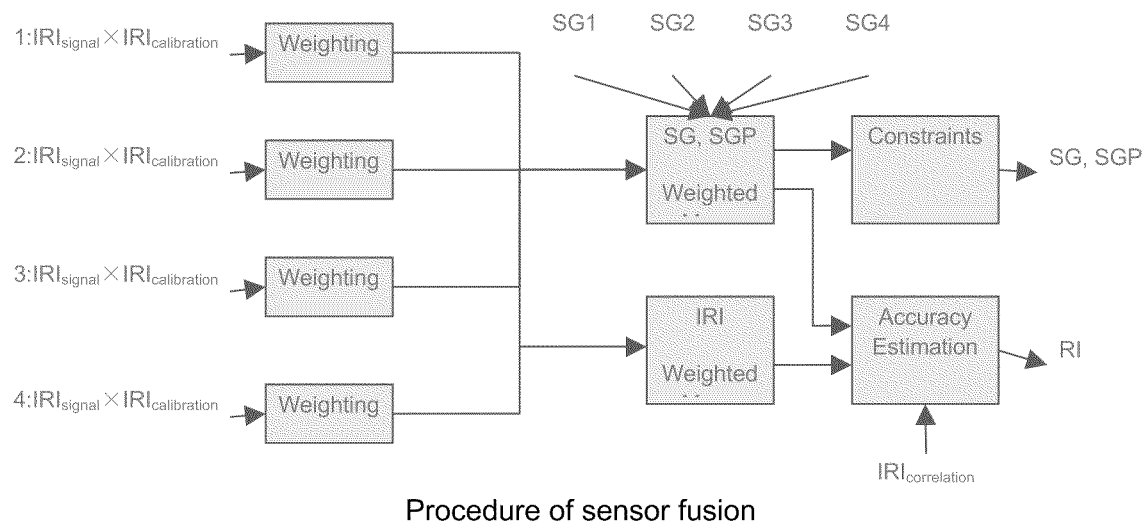
FIG. 6C provides a flowchart showing a procedure of sensor fusion. For each signal sampling time, each sensor's IRI_signal and IRI_calibration are used to generate a fusion weighting.

FIG. 6A shows the illustrative functionalities and inputs/outputs of an illustrative ICF (Integrity Check, Calibration scheme, sensor Fusion) module. All the signals from the two groups of sensors will be processed by ICF. Thus, four Isig signals and four Vcntr signals, will be fed into the ICF for processing. Except for the signals, discrete blood glucose (BG) values measured by human operators will also be fed into the ICF for the purpose of sensor calibration.

The ICF will output three variables. The first is the calculated sensor glucose (SG) value. The second is a quad sensor status (QSS) indicting the status of the whole sensor set. The possible values of the sensor status are "pending", "good", "bad", "failed". Finally, a reliability index (RI) will also be calculated to indicate how reliable the sensor's glucose reading is. The numerical range of the RI will be from 0 to 1, where 0 means that the quad sensor does not work and 1 means that the quad sensor works perfectly.

The functionalities of ICF include:
Integrity Check: check the sensors' integrity and monitor the status of the quad sensor.
Calibration Scheme: convert each sensor's signal to glucose value
Sensor Fusion: fuse the data from different sensors to improve accuracy and achieve multi-sensor redundancy ICF Workflow Throughout the sensor life time, the working of the ICF can be roughly divided into three stages temporally: initialization check; stabilization check; sensor monitoring and glucose calculation. The sensors need to be initialized before they can be used to detect glucose levels. A set of high-amplitude pulses will be used to initialize the sensor. By checking the sensor's response to the pulses in initialization check, we can tell how healthy the sensor is.

Because of the high amplitude pulses, the sensors may need to go through a stabilization period before they can fully go back to the normal status. Stabilization check will be performed during this period to ensure that the sensors do go back to the normal status. If at least one of the sensors is judged to be in normal status, the algorithm will consider the quad-sensor to be ready to work.

During the normal working status, the algorithm will take in the sensor signal and convert the signal into sensor glucose reading, with the reference of the blood glucose. Simultaneously, the algorithm will monitor the sensor health status by signal analysis. The health status of each sensor will supply as the foundation for the final sensor fusion to yield a single sensor glucose (SG), a reliability index (RI) and a quad-sensor status (QSS).

Integrity Check

The purpose of integrity check can be three fold: (a) Check the sensor integrity and monitor the status of the quad-sensor; (b) Enable the sensor fusion; and (c) Estimate the sensor accuracy.

Integrity will be checked for each of the four sensors as well as for the quad-sensor as a unit, throughout the sensor life. Temporally sequential parts of the integrity check include a initialization check, stabilization check and sensor monitoring. Different signal features are extracted in different stage to facilitate the judgment of the integrity. For example, the signal amplitude bound check, trend, noise and correlation features are all extracted during sensor monitoring. These features are then used to generate a set of internal reliability indexes (IRIs) as well as the sensor status (SS). The IRIs are used to tell the status of each sensor as well as the quad-sensor: RI and QSS are generated based on the IRIs.

Initialization Check

After the insertion of the sensors, there is a period allowed for the sensors to be wet, be initialized and recover from initialization. Initialization check will be performed at the end of this period for each of the sensors. Initialization check is performed in two steps: the first step is the bound check and the second step is the recovery analysis. The bound check ensures that the maximum of the Isig, the mean of the Isig and the standard deviation of the Isig are large enough, which means that the sensor must respond well to the high-amplitude pulses. The recovery analysis ensures that the Isig signal does not stay at high level after the initialization.

The QSS is set to "pending" during this period. If at least one FSS passes the initialization check, the system will proceed with the QSS still as "pending". The sensors that do not pass the initialization check still have the chance to come back to workflow later on if the sensors' status is determined to be "good". If none of the full-size sensors passes initialization check, ICF will set QSS to "failed". The system control logic will alert "Sensor Replacement" accordingly.

Stabilization Check

If the quad-sensor passes initialization check, a stabilization period with a predetermined maximum time is allowed for the sensors to stabilize. Accordingly, a stabilization check will be performed based on the IRIs during this period. The stabilization check will perform bound check for each of the sensors to ensure the Isig and Vcntr values both fall in pre-defined ranges. The absolute rate of change for Isig and Vcntr are also checked to ensure there is no exotic behavior in the signal. If the signal of a sensor well behaves for a certain time, the sensor status will be set to "good". If at least one FSS passes stabilization check, the system will proceed with these sensors and the QSS will be set to "good". The sensors that do not pass stabilization check still have the chance to come back to workflow later on if the sensor's status is determined to be "good". If none of the full-range sensors passes stabilization check, ICF will set QSS to "failed". The system control logic will alert "Sensor Replacement" accordingly.

IRI Calculation

After passing initialization check and stabilization check, the quad-sensor will start working. A set of internal reliability indexes (IRIs) are calculated at each signal sampling time to monitor the sensor status. The IRIs are: IRI_system calculation, which is essentially, bound check. IRI_system is calculated based on the single sensor signal. IRI_signal calculation includes noise level, trend estimation and signal change check. IRI_signal is calculated based on the single sensor signal. IRI_calibration, which measures the correlation of signal vs. BG, indicates if the signal is following the BG. IRI_calibration is calculated based on the single sensor signal and BG input by the user. IRI_correlation, which measures the correlation between the signals of a pair of sensors, indicates our confidence in the quad-sensor—the higher the correlation between the sensors, the higher confidence we have in the quad-sensor.

IRI_system

IRI_system is essentially bound check. The Isig value, the Vcntr value, the Isig rate of change, the Vcntr rate of change are compared with a set of pre-defined thresholds to determine if they are out-of-bound. The thresholds may be different for FSS and HSS. When the signal is within bounds, IRI_system will be 1. When the signal is out-of-bounds, IRI_system will be 0.

IRI_signal

The calculation procedure of IRI_signal is shown in FIG. 6B. Isig and Vcntr will go through signal analysis to yield a set of metrics. The metrics are finally fused together with IRI_system to yield IRI_signal. This calculation will be performed at each sampling time.

Isig Noise Level Measurement

There are many methods to measure noise level in the Isig. In method 1, signal decomposition methods such as wavelet, empirical mode decomposition are used to decompose the Isig to signal and noise. Then the power of the noise and signal can be used to calculate the noise level. In method 2, low pass filters such as FIR (including Savitzky-Golay filter), IIR are used to filter the Isig. The difference between filtered signal and original signal is considered as an indicator for noise level. In method 3, singular spectral analysis (SSA) is used to estimate the Isig noise level. In SSA, lag-covariance matrix of the signal is first constructed based on the raw signal. Noise level can then be estimated through eigen analysis of the lag-covariance matrix. All the above method can yield relatively accurate noise level estimation Sensor Fusion A procedure of sensor fusion is shown in FIG. 6C. For each signal sampling time, each sensor's IRI_signal and IRI_calibration are used to generate a fusion weighting based on a formula such as the following (see, e.g. U.S. application Ser. No. 12/914,969, the contents of which are incorporated herein by reference):

$$W_i = -\frac{1}{\log(IRI\_signal_i \times IRI\_calibrtion_i + c)}$$

Where c is a constant to ensure the weighting W is valid.

Using the fusion weight, the weighted mean of all the sensors' SG and SGP are calculated and constrained by the physiological limit. This procedure will yield the final SG and SGP for the quad sensor. The IRIs (IRI_signal×IRI_calibration) will go through the same weighted mean procedure to yield a middle value FRI. FRI is further updated by a formula such as the following (see, e.g. U.S. application Ser. No. 12/914,969, the contents of which are incorporated herein by reference):

$$FRI(n) = FRI(n) \times \frac{1 + IRI\_correlation(n)}{2}$$

In order to make the final reliability index (RI) an indicator of the sensor accuracy, the mean absolute relative difference (ARD) of the last several BG entries vs. SG are collected:

$$ARD_i = \frac{|BG_i - SG_i|}{SG_i}$$

Where i are the indexes for the last several BG entries.

So the reference ARD ArdRef for the current point is calculated as following:

$$ArdRef(n) = \frac{\sum_i u_i \times ARD_i}{\sum_i u_i}$$

Where: $u_i = 1 - IRI\_correlation(i)$

And the reference reliability index RIRef for the current point is calculated as following:

$$RIRef(n) = \frac{\sum_i u_i \times FRI_i}{\sum_i u_i}$$

Finally, the RI is calculated as:

$$RI = 1 - ArdRef \times \left(1 - \frac{FRI(n) - RIRef}{RIRef}\right)$$

Example 3

Glucose Monitoring Systems Exhibiting Enhanced Performance in the Critically Ill The disclosure provided herein provides methods and materials for combining sensor readings to give a single output. The performance of most continuous monitoring sensors today is characterized by the mean absolute relative difference (MARD). Using this criteria, the above-noted sensor structures (in which each patient had two sensors) in combination with the algorithms designed for use with such structures were shown to exhibit surprising good properties. Specifically, the individual sensor performance was at about 16% MARD. With the algorithms disclosed herein where the sensor data is combined (by for example, determining a mean value for a signal obtained from the multiple electrode arrays; and/or determining a standard deviation for a signal obtained from the multiple electrode arrays), then assessed for performance, which showed an 11% MARD; a significant difference.

Methods:

A study was conducted in a cardiothoracic ICU at the University of Michigan under IRB approval. The investigational sensors were a modified version of the Medtronic SOF-SENSOR™ (Medtronic; Northridge, Calif.). The modifications focused on interference rejection and increased sensitivity to low glucose.

Each subject wore two modified sensors attached to a recording device that collected sensor signals in one-minute intervals. During post-processing, the two sensor signals from each patient were combined to produce a single glucose value output. Reference blood glucose information was collected by ACCU-CHEK® meter (Roche Diagnostics, Mannhein Germany) on an hourly basis, by arterial draw or by capillary sampling. APACHE II score was assessed on a daily basis, and concomitant medication information was collected with time of delivery for post-study analysis.

Results:

15 surgical patients were enrolled and completed the study. The average daily APACHE II score for the patient group was 20 (range: 4-67). During the study, 512 paired data points between sensor glucose and reference blood glucose were recorded. The Mean Absolute Relative Difference between paired points was 11.0%. The ISO 15197 bias analysis showed 100% of paired points with glucose<75 mg/dl within 15 mg/dl (n=5), and 87% of paired points with glucose>75 mg/dl within the 20% error range. A total of 110 medications were administered and evaluated during the course of this study. Analysis of sensor signal after medication delivery, including acetaminophen, showed no indication of interference with glucose signal.

Conclusions:

The modified sensor showed good agreement with reference glucose and no drug interference issues in the patients studied. Although a small feasibility study, the results indicate that specialized interstitial glucose sensors provide a promising tool for glucose monitoring in the hospital.

Example 4

Illustrative Glucose Sensor Signal Drift Detection Methods

The subcutaneous glucose sensor measures the glucose level in the body fluid. The electro-chemical glucose sensors generate current at nA level. The amplitude of the current will change based on the glucose level thus glucose measurement is performed. The glucose sensors are designed to stay in the body for several days. However, some sensors' signal will gradually drift down (or up) and finally die out due to sensor defects or environmental factors. One of the tasks of sensor fault detection is thus to detect the drifting of the signal, in spite of the physiological activity.

The problem of drift detection can be solved in two steps. The first step is trend estimation, where the fundamental long term trend of the signal is estimated. The second step is the real-time logic to judge whether an estimated trend indicates the drifting of the signal.

Trend Estimation

Three methods are considered for trend estimation: empirical mode decomposition, wavelet decomposition and iterative trend estimation.

Empirical Mode Decomposition (EMD)

Empirical Mode Decomposition (EMD) is the first step of Hilbert-Huang Transform (HHT) (SEE, E. G. Norden E. Huang, Nii O. Attoh-Okine, The Hilbert-Huang Transform in Engineering. CRC Press, First Edition, Jun. 23, 2005), which is designed to perform instantaneous frequency estimation for nonlinear non-stationary signals. EMD is used for signal decomposition in HHT. In EMD, spline functions are used to gradually remove details from the original signal. The procedure is repeated until a monotonic curve or a curve with only one extreme value is left. The final monotonic smooth curve is considered as the estimated fundamental trend of the signal.

A linear regression is performed on the monotonic smooth curve. The slope of the linear regression is considered as the quantitative measurement Tr of the signal.

Wavelet Decomposition

In wavelet decomposition, discrete wavelet transform DWT (Ingrid Daubechies, Ten Lectures on Wavelets. CBMS-NSF Regional Conference Series in Applied Mathematics. SIAM Press, First Edition, Jun. 1, 1992) is used to decompose the signals into different levels of details. The level with smoothest signal is approximation signal, which is reconstructed from approximation coefficients calculated from DWT. The smooth signal reconstructed from approximation coefficients is considered as the estimated fundamental trend of the signal. A linear regression is performed on the approximation signal. The slope of the linear regression is considered as the quantitative measurement Tr of the signal.

Iterative Trend Estimation

In iterative trend estimation, the trend at each signal sample n is iteratively calculated based on the trend at the previous signal sample n−1. The initial trend can be estimated by linear regression. The slope of the linear regression is considered as initial trend Tr(0). The intercept is considered as initial growth G(0). The trend at every point is then estimated as:

$$Tr(n)=Tr(n-1)+Wg \times G(n-1)$$

Where G(n) is the growth term and Wg is the growth parameter that is determined empirically. G(n) is iteratively updated as well:

$$G(n)=Wg \times G(n-1)+Wt \times [sig(n)-Tr(n)]$$

Where Wt is the trend parameter that is determined empirically.

Real Time Logic for Drift Detection

The second step is the real-time logic to judge whether an estimated trend Tr(n) at signal sample n indicates the drifting of the signal. The trend can be estimated by any of the above signals. Two positive thresholds T1 and T2 are used for drift detection, where T1<T2. When the absolute value of Tr(n) is less than T1, the sensor trend is considered as in normal fluctuation. No drifting is declared. When the absolute value of Tr(n) is between T1 and T2, drifting is declared. The severity of drifting is measured by the following drifting metric:

$$MetDrift = \frac{abs[Tr(n)] - T1}{T2 - T1}$$

The drifting factor MetDrift has a value range between 0 and 1. The larger the drifting factor F, the more severe the drifting. When the absolute value of Tr(n) is greater than T2, the sensor is declared dying due to severe drifting.

The invention claimed is:

1. An amperometric analyte sensor system comprising:
a probe platform;
a first probe coupled to the probe platform and adapted to be inserted in vivo, wherein the first probe comprises:
   a first electrode array comprising a working electrode, a counter electrode and a reference electrode; and
   a second electrode array comprising a working electrode, a counter electrode and a reference electrode;
a second probe coupled to the probe platform and adapted to be inserted in vivo, wherein the second probe comprises:
   a third electrode array comprising a working electrode, a counter electrode and a reference electrode; and
   a fourth electrode array comprising a working electrode, a counter electrode and a reference electrode;
wherein the first, second, third and fourth electrode arrays are configured to be electronically independent of one another; and
the system further comprises:
   a processor;
   a computer-readable program code having instructions, which when executed cause the processor to:
   assess signal data obtained from each of the first, second, third and fourth electrode arrays against one or more reliability parameters;
   rank signal data from each of the first, second, third and fourth electrode arrays in accordance with the assessment against the one or more reliability parameters; and
   compute an analyte concentration based upon the ranking of signal data obtained from each of the first, second, third and fourth electrode arrays.

2. The amperometric analyte sensor system of claim 1, wherein:
the first and second electrode arrays are disposed at different locations along the first probe so that the first and second electrode arrays are located at different depths when inserted into an in vivo environment; or
the third and fourth electrode arrays are disposed at different locations along the second probe so that the third and fourth electrode arrays are located at different depths when inserted into an in vivo environment.

3. The amperometric analyte sensor system of claim 1, wherein the system further comprises an adhesive patch adapted to secure the probe platform to the skin of a patient.

4. The amperometric analyte sensor system of claim 1, wherein one or more electrodes in the first electrode array, the second electrode array, the third electrode array and the fourth electrode array are coated with a plurality of layered materials comprising:
an interference rejection layer;
an analyte sensing layer;
a protein layer;
an adhesion promoting layer; and
an analyte modulating layer, wherein the analyte modulating layer comprises a composition that modulates the diffusion of an analyte diffusing through the analyte modulating layer.

5. The amperometric analyte sensor system of claim 4, wherein the interference rejection layer comprises crosslinked primary amine polymers having an average molecular weight between 4 and 500 kilodaltons; or crosslinked Poly(2-hydroxyethyl methacrylate) polymers having an average molecular weight between 100 and 1000 kilodaltons.

6. The amperometric analyte sensor system of claim 4, wherein the analyte modulating layer comprises a blended mixture of:
a linear polyurethane/polyurea polymer, and
a branched acrylate polymer; and
the linear polyurethane/polyurea polymer and the branched acrylate polymer are blended at a ratio of between 1:1 and 1:20 by weight %.

7. The amperometric analyte sensor system of claim 1, wherein: electrodes in the first electrode array and the third electrode array:
   (a) comprise a platinum having a first set of material properties; or
   (b) are coated with a first set of layered materials; and
electrodes in the second electrode array and the fourth electrode array:
   (c) comprise platinum having a second set of material properties; or
   (d) are coated with a second set of layered materials.

8. The amperometric analyte sensor system of claim 1, wherein the size of the working electrodes in the first and third electrode arrays are at least 1.5, 2 or 2.5 fold larger that the size of working electrodes in the second and fourth electrode arrays.

9. The amperometric analyte sensor system of claim 1, wherein the first, second, third and fourth electrode arrays generate:
a current signal (Isig), wherein the current signal comprises a signal generated by the first, second, third or fourth electrode arrays in the presence of an analyte; and
a voltage signal (Vcntr), wherein the voltage signal comprises a signal generated by the first, second, third or fourth electrode arrays in response to voltage applied to the first, second, third or fourth electrode array.

10. The amperometric analyte sensor system of claim 1, further comprising a monitor adapted to display signal information.

11. The amperometric analyte sensor system of claim 1, wherein a reliability parameter is calculated by a method comprising:
   determining whether a signal amplitude falls within a predetermined range of amplitudes;
   determining a trend in sensor signals from a plurality of signals sensed by an electrode array;
   determining an amount of nonspecific signal noise sensed by an electrode array;
   determining a mean value for a signal obtained from the first, second, third and fourth electrode arrays; and/or
   determining a standard deviation for a signal obtained from the first, second, third or fourth electrode arrays.

12. The amperometric analyte sensor system of claim 1, wherein:
   signal data obtained from each of the first, second, third and fourth electrode arrays is weighted according to one or more reliability parameters; and
   the weighted signal data is fused to compute an analyte concentration.

13. The amperometric analyte sensor system of claim 1, wherein signal data from each of the first, second, third and fourth electrode arrays is assessed so as to provide an indication of the reliability of a signal obtained from one or more of the first, second, third and fourth electrode arrays.

14. The amperometric analyte sensor system of claim 1, wherein the processor further calculates a reliability index, wherein the reliability index provides an estimation of the reliability of the analyte concentration computed by the system.

15. The amperometric analyte sensor system of claim 1, wherein:
   the analyte sensed is glucose;
   at least one electrode array is constructed from materials designed to predominantly sense glucose at a concentration range of 40-100 mg/dL; and
   at least one electrode array is constructed from materials designed to predominantly sense glucose at a concentration range of 70-400 mg/dL.

16. The amperometric analyte sensor system of claim 1, wherein:
   the analyte sensed is glucose;
   at least one electrode array is constructed from materials designed to sense signals resulting from the presence of glucose; and
   at least one electrode array is constructed from materials designed to sense:
      (a) signals resulting from background noise; or
      (b) signals resulting from interfering compounds.

17. The amperometric analyte sensor system of claim 1, wherein:
   the processor evaluates signal data so as to provide evidence of signal drift over time in the amperometric analyte sensor system; or
   the processor evaluates signal data so as to provide information on the hydration of the amperometric analyte sensor system.

18. The amperometric analyte sensor system of claim 17, wherein the processor evaluates data resulting from a plurality of amplitude pulses applied to the system.

19. A method for sensing glucose concentrations in a diabetic patient, the method comprising:
   observing signal data generated by a first, second, third and fourth electrode arrays in the presence of glucose in an amperometric analyte sensor system comprising:
      a probe platform;
      a first probe coupled to the probe platform and adapted to be inserted in vivo, wherein the first probe comprises:
         a first electrode array comprising a working electrode, a counter electrode and a reference electrode; and
         a second electrode array comprising a working electrode, a counter electrode and a reference electrode;
      a second probe coupled to the probe platform and adapted to be inserted in vivo, wherein the second probe comprises:
         a third electrode array comprising a working electrode, a counter electrode and a reference electrode; and
         a fourth electrode array comprising a working electrode, a counter electrode and a reference electrode;
   wherein the first, second, third and fourth electrode arrays are configured to be electronically independent of one another; and the method further comprises
   comparing the signal data from each of the first, second, third and fourth electrode arrays; and
   computing an analyte concentration using the comparison of the signal data obtained from each of the first, second, third and fourth electrode arrays.

20. The method of claim 19, wherein the system comprises a processor for comparing the signal data from each of the first, second, third and fourth electrode arrays and the comparison includes:
   observing whether a signal obtained from each of the first, second, third and fourth electrode arrays falls within a predetermined range of values;
   observing a trend in sensor signal data from each of the first, second, third and fourth electrode arrays; or
   observing an amount of nonspecific signal noise in each of the first, second, third and fourth electrode arrays.

21. The method of claim 20, wherein the comparison is used to identify a signal from an array that is:
   indicative of increasing glucose blood concentrations or decreasing blood glucose concentrations in the diabetic patient;
   indicative of insufficient sensor hydration;
   indicative of sensor signal drift; or
   indicative of sensor loss of sensitivity to glucose.

22. The method of claim 20, further comprising:
   weighing signal data obtained from each of the first, second, third and fourth electrode arrays; and
   using weighted signal data to compute an analyte concentration.

23. The method of claim 22, further comprising using the processor to:
   assess signal data from each of the first, second, third and fourth electrode array; and
   generate reliability index that indicates the reliability of a signal obtained from one or more of the first, second, third and fourth electrode arrays.

24. The method of claim 20, wherein one or more electrodes in the first electrode array, the second electrode array, the third electrode array and the fourth electrode array are coated with a plurality of layered materials comprising:
   an interference rejection layer;
   an analyte sensing layer;
   a protein layer;
   an adhesion promoting layer; and
   an analyte modulating layer, wherein the analyte modulating layer comprises a composition that modulates the diffusion of an analyte diffusing through the analyte modulating layer.

* * * * *